(12) United States Patent
Amin et al.

(10) Patent No.: US 6,265,415 B1
(45) Date of Patent: Jul. 24, 2001

(54) COMPOUNDS FOR INHIBITION OF GASTRIC ACID SECRETION

(75) Inventors: Kosrat Amin; Mikael Dahlström, both of Mölndal; Peter Nordberg, Sävedalen; Ingemar Starke, Göteborg, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/043,040

(22) PCT Filed: Feb. 17, 1998

(86) PCT No.: PCT/SE98/00275
§ 371 Date: Mar. 10, 1998
§ 102(e) Date: Mar. 10, 1998

(87) PCT Pub. No.: WO98/37080
PCT Pub. Date: Aug. 27, 1998

(30) Foreign Application Priority Data
Feb. 25, 1997 (SE) .................................. 9700661

(51) Int. Cl.⁷ ..................... A61K 31/437; C07D 471/04; A61P 1/04
(52) U.S. Cl. ............................ 514/300; 546/121
(58) Field of Search .............. 546/121; 514/300

(56) References Cited

FOREIGN PATENT DOCUMENTS 0033094  10/1984  (EP).
0204285  12/1986  (EP).

OTHER PUBLICATIONS

J. Med. Chem., vol. 34, 1991, James J. Kaminiski et al., "Antiulcer Agents. 5. Inhibition of Gastric H+/K+–ATPase by Substituted Imidazo[1,2–a]pyridines and Related Analogues and Its Implication in Modeling the High Affinity Potassium Ion Binding Site of the Gastric Proton Pump Enzyme", pp. 533–541.

J. Med. Chem., vol. 32, 1989, James J. Kaminiski et al., "Antiulcer Agents. 5. Conformational Considerations and the Antiulcer Activity of Substituted Imidazo[1,2–a]pyridines and Related Analogues", pp. 1686–1700.

J. Med. Chem., vol. 30, 1987, James J. Kaminski et al., "Antiulcer Agents. 3. Structure–Activity–Toxicity Relationships of Substituted Imidazo[1,2–a]pyridines and a Related Imidazo 9 (1,2–a) pyrazine", pp. 2047–2051.

J. Med. Chem., vol. 30, 1987, James J. Kaminski et al., "Antiulcer Agents. 2. Gastric Antisecretory, Cytoprotective, and Metabolic Properties of Substituted Imidazo[1,2–a] pyridines and Analogues", pp 2031–2046.

J. Med. Chem., vol. 28, 1985, James J. Kaminiski et al., "Antiulcer Agents. 1. Gastric Antisecretory and Cytoprotective Properties of Substituted Imidazo[1,2–a]pyridines", pp. 876–892.

Annu. Rev. Pharmacol. Toxico., 1995, George Sachs et al., "The Pharmacology of the Gastric Acid Pump: the H+, K+ ATPase", vol. 35; 277–305.

*Primary Examiner*—Evelyn Mei Huang
(74) *Attorney, Agent, or Firm*—White & Case LLP

(57) ABSTRACT

The present invention relates to imidazo pyridine derivatives of the formula (I), in which the phenyl moiety is substituted with lower alkyl in 2- and 6-position, which inhibit exogenously or endogenously stimulated gastric acid secretion and thus can be used in the prevention and treatment of gastrointestinal inflammatory diseases.

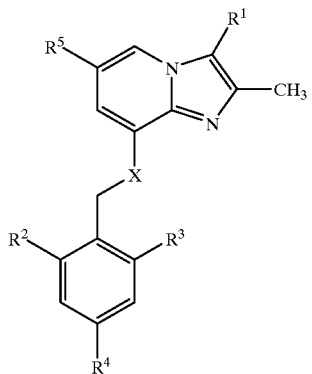

33 Claims, No Drawings

COMPOUNDS FOR INHIBITION OF GASTRIC ACID SECRETION

This application is the national phase of PCT/SE98/00275, filed Feb. 17, 1998.

TECHNICAL FIELD

The present invention relates to novel compounds, and therapeutically acceptable salts thereof, which inhibit exogenously or endogenously stimulated gastric acid secretion and thus can be used in the prevention and treatment of gastrointestinal inflammatory diseases. In further aspects, the invention relates to compounds of the invention for use in therapy; to processes for preparation of such new compounds; to pharmaceutical compositions containing at least one compound of the invention, or a therapeutically acceptable salt thereof, as active ingredient; and to the use of the active compounds in the manufacture of medicaments for the medical use indicated above.

BACKGROUND ART

Substituted imidazo[1,2-a]pyridines, useful in the treatment of peptic ulcer diseases, are known in the art, e.g. from EP-B-0033094 and U.S. Pat. No. 4,450,164 (Schering Corporation); from EP-B-0204285 and U.S. Pat. No. 4,725,601 (Fujisawa Pharmaceutical Co.); and from publications by J. J. Kaminski et al. in the Journal of Medical Chemistry (vol. 28, 876–892, 1985; vol. 30, 2031–2046, 1987; vol. 30, 2047–2051, 1987; vol. 32, 1686–1700, 1989; and vol. 34, 533–541, 1991).

An imidazo pyridine derivative being substituted in 8-position with 2,4,6-$(CH_3)_3$—$C_6H_2CH_2O$ is disclosed in EP-B-0033094 and as "Compound No. 49" in Kaminski et al., J. Med. Chem. vol. 28, 876–892, 1985. However, according to the latter publication, the said compound did not show favorable characteristics when tested as an inhibitor of gastric acid secretion.

For a review of the pharmacology of the gastric acid pump (the $H^+$, $K^+$-ATPase), see Sachs et al. (1995) Annu. Rev. Pharmacol. Toxicol. 35: 277–305.

DISCLOSURE OF THE INVENTION

It has surprisingly been found that compounds of the Formula I, which are substituted imidazo pyridine derivatives in which the phenyl moiety is substituted with lower alkyl in 2- and 6-position, are particularly effective as inhibitors of the gastrointestinal $H^+$, $K^+$-ATPase and thereby as inhibitors of gastric acid secretion.

In one aspect, the invention thus relates to compounds of the general Formula I:

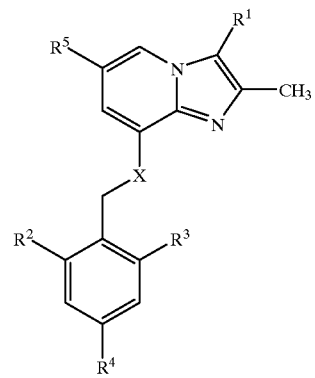

or a pharmaceutically acceptable salt thereof, wherein
$R^1$ is $CH_3$ or $CH_2OH$;
$R^2$ is lower alkyl;
$R^3$ is lower alkyl;
$R^4$ is H or halogen;
$R^5$ is H, halogen, or lower alkyl;
X is NH or O.

As used herein, the term "lower alkyl" denotes a straight or branched alkyl group having from 1 to 6, preferably 1 to 4, carbon atoms. Examples of "lower alkyl" include methyl, ethyl, n-propyl, iso-propyl, n-butyl, iso-butyl, sec-butyl, t-butyl and straight- and branched-chain pentyl and hexyl. Preferably, "lower alkyl" means methyl, ethyl, n-propyl, iso-propyl, n-butyl, iso-butyl, sec-butyl and t-butyl.

The term "halogen" includes fluoro, chloro, bromo and iodo.

Both the pure enantiomers, racemic mixtures and unequal mixtures of two enantiomers are within the scope of the invention. It should be understood that all the diastereomeric forms possible (pure enantiomers, racemic mixtures and unequal mixtures of two enantiomers) are within the scope of the invention. Also included in the invention are derivatives of the compounds of the Formula I which have the biological function of the compounds of the Formula I.

Depending on the process conditions the end products of the Formula I are obtained either in neutral or salt form. Both the free base and the salts of these end products are within the scope of the invention.

Acid addition salts of the new compounds may in a manner known per se be transformed into the free base using basic agents such as alkali or by ion exchange. The free base obtained may also form salts with organic or inorganic acids.

In the preparation of acid addition salts, preferably such acids are used which form suitably therapeutically acceptable salts. Examples of such acids are hydrohalogen acids such as hydrochloric acid, sulfuric acid, phosphoric acid, nitric acid, aliphatic, alicyclic, aromatic or heterocyclic carboxyl or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybensoic acid, embonic acid, methanesulfonic acid, ethanesulfonic acid, hydroxyethanesulfonic acid, halogenbensenesulfonic acid, toluenesulfonic acid or naphthalenesulfonic acid.

Preferred compounds according to the invention are those of the Formula I wherein $R^2$ is $CH_3$ or $CH_2CH_3$; $R^3$ is $CH_3$ or $CH_2CH_3$; $R^4$ is H, Br, Cl or F; and $R^5$ is H, $CH_3$, Br, Cl or F, more preferably H, $CH_3$, or F.

Particularly preferred compounds according to the invention are:
8-(2,6-dimethylbenzylamino)-2,3,6-trimethylimidazo[1,2-a]pyridine;
8-(2,6-dimethylbenzylamino)-3-hydroxymethyl-2-methylimidazo[1,2-a]pyridine;
2,3-dimethyl-8-(2,6-dimethyl-4-fluorobenzylamino) imidazo[1,2-a]pyridine;
2,6-dimethyl-8-(2,6-dimethylbenzylamino)-3-hydroxymethyl imidazo[1,2-a]pyridine;
2,6-dimethyl-8-(2,6-dimethyl-4-fluorobenzylamino)-3-hydroxymethylimidazo[1,2-a]pyridine;
8-(2,6-dimethyl-4-fluorobenzylamino)-2,3,6-trimethyl imidazo[1,2-a]pyridine;
2,3-dimethyl-8-(2,6-dimethyl-4-chlorobenzylamino) imidazo[1,2-a]pyridine;
2,6-dimethyl-8-(2-ethyl-6-methylbenzylamino)-3-hydroxymethylimidazo[1,2-a]pyridine;
8-(2,6-diethylbenzylamino)-2,6-dimethyl-3-hydroxymethylimidazo[1,2-a]pyridine;
8-(2-ethyl-6-methylbenzylamino)-2,3,6-trimethylimidazo [1,2-a]pyridine;
8-(2,6-dimethyl-4-fluorobenzyloxy)-3-hydroxymethyl-2-methylimidazo[1,2-a]pyridine;
2,6-dimethyl-8-(2,6-dimethylbenzyloxy)-3-hydroxymethylimidazo[1,2-a]pyridine;
2,6-dimethyl-8-(2-ethyl-4-fluoro-6-methylbenzylamino)-3-hydroxymethylimidazo[1,2-a]pyridine;
8-(2-ethyl-4-fluoro-6-methylbenzylamino)-2,3,6-trimethylimidazo[1,2-a]pyridine.

Preparation

The present invention also provides the following processes A, B, C, D, and E for the manufacture of compounds with the general Formula I.

Process A

Process A for manufacture of compounds with the general Formula I comprises the following steps:
Compounds of the general Formula II

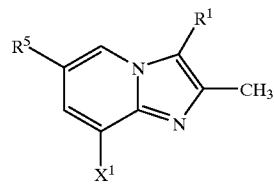

II wherein $X^1$ is $NH_2$ or OH, and $R^1$ and $R^5$ are as defined for Formula I, can be reacted with compounds of the general Formula III

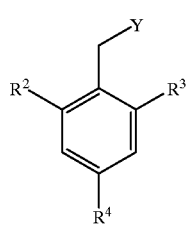

III wherein $R^2$, $R^3$ and $R^4$ are as defined for Formula I and Y is a leaving group, such as a halide, tosyloxy or mesyloxy, to the compounds of the Formula I.

It is convenient to conduct this reaction in an inert solvent, e.g. acetone, acetonitrile, dimethoxyethane, methanol, ethanol or dimethylformamide with or without a base. The base is e.g. an alkali metal hydroxide, such as sodium hydroxide and potassium hydroxide; an alkali metal carbonate, such as potassium carbonate and sodium carbonate; or an organic amine, such as triethylamin.

Process B

Process B for manufacture of compounds with the general Formula I, wherein X is NH, comprises the following steps:
Compounds of the general Formula IV

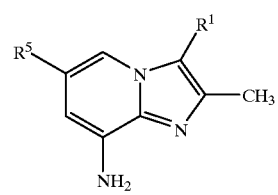

IV wherein $R^1$ and $R^5$ are as defined for Formula I, can be reacted with compounds of the general Formula V

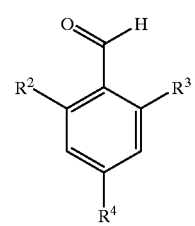

V wherein $R^2$, $R^3$ and $R^4$ are as defined for Formula I, in the presence of a Lewis acid e.g. zinc chloride to the compounds of the Formula VI

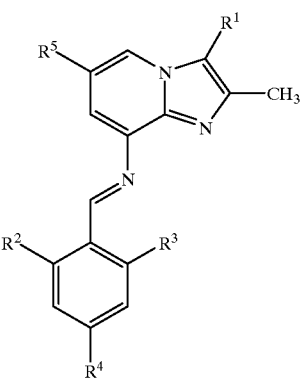

VI wherein $R^1$, $R^2$, $R^3$, $R^4$ and $R^5$ are as defined for Formula I, whereupon the compounds of the general Formula VI are reduced e.g. by using sodiumborohydride or sodiumcyano borohydride to compounds of the general Formula I wherein X is NH. The reactions can be carried out under standard conditions in an inert solvent e.g. methanol or ethanol.

Process C

Process C for manufacture of compounds with the general Formula I, wherein $R^1$ is $CH_2OH$, comprises the following steps:

Compounds of the general Formula VII

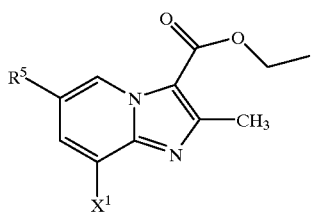

VII wherein $X^1$ is $NH_2$ or OH and $R^5$ are as defined for Formula I, can be reacted with compounds of the general Formula III

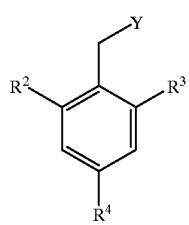

III wherein $R^2$, $R^3$ and $R^4$ are as defined for Formula I and Y is a leaving group, such as a halide, tosyloxy or mesyloxy, to the compounds of the Formula VIII

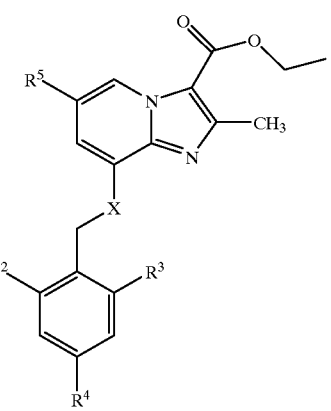

VIII wherein $R^2$, $R^3$, $R^4$, $R^5$ and X is as defined for Formula I.

It is convenient to conduct this reaction in an inert solvent, e.g. acetone, acetonitrile, dimethoxyethane, methanol, ethanol or dimethylformamide with or without a base. The base is e.g. an alkali metal hydroxide, such as sodium hydroxide and potassium hydroxide; an alkali metal carbonate, such as potassium carbonate and sodium carbonate; or an organic amine, such as triethylamin.

Reduction of compounds of the general Formula VIII, e.g. by using lithium aluminium hydride in tetrahydrofuran or ether yields the compounds of the general Formula I wherein $R^1$ is $CH_2OH$.

Process D

Process D for manufacture of compounds with the general Formula I, wherein $R^1$ is $CH_2OH$ and X is NH comprises the following steps:

Compounds of the Formula IX

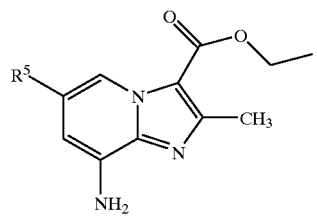

IX wherein $R^5$ is as defined for Formula I, can be reacted with compounds of the general Formula V

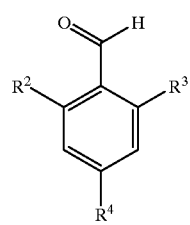

V wherein $R^2$, $R^3$ and $R^4$ are as defined for Formula I, in the presence of a Lewis acid e.g. zinc chloride to the compounds of the Formula VI

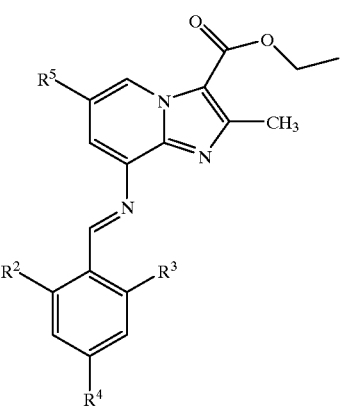

X wherein $R^2$, $R^3$, $R^4$ and $R^5$ are as defined for Formula I, whereupon the compounds of the general Formula X are reduced e.g. by using sodium borohydride or sodiumcyano borohydride to compounds of the general Formula XI

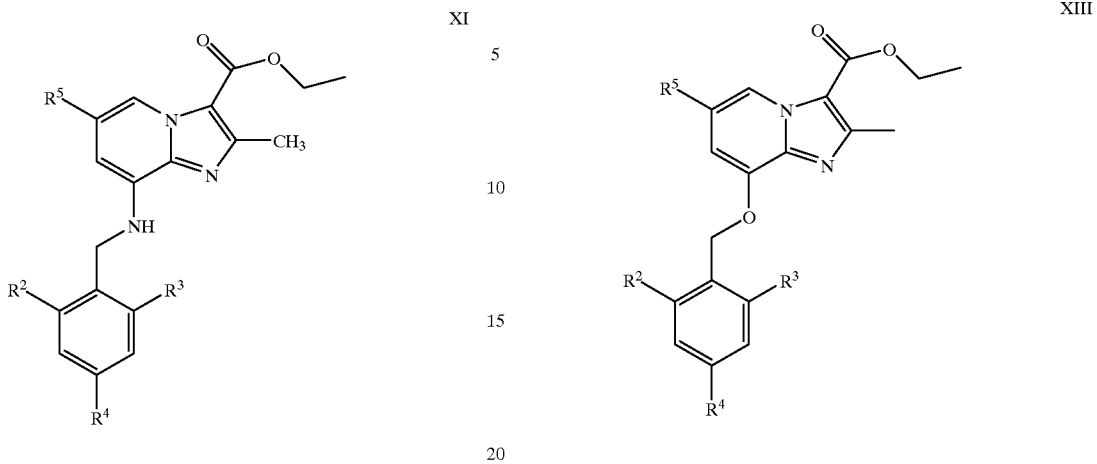

wherein $R^2$, $R^3$, $R^4$ and $R^5$ are as defined for Formula I. The reactions can be carried out under standard conditions in an inert solvent e.g. methanol or ethanol.

Reduction of compounds of the general Formula XI e.g. by using lithium aluminium hydride in tetrahydrofuran or ether yields the compounds of the general Formula I wherein $R^1$ is $CH_2OH$ and X is NH.

Process E

Condensation of compounds of the general Formula XII

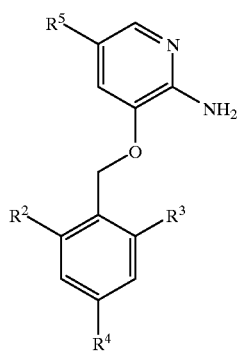

wherein $R^2$, $R^3$, $R^4$, and $R^5$ are as defined for Formula I, with α-halocarbonyl intermediates of the general formula $CH_3COCH(Z)COOCH_2CH_3$ wherein Z is Br or Cl, in an inert solvent e.g. acetonitrile or ethanol results in formation of compounds of the general Formula XIII wherein $R^2$, $R^3$, $R^4$, and $R^5$ are as defined for Formula I Reduction of compounds of the general Formula XIII e.g. by using lithium aluminium hydride in tetrahydrofuran or ether yields the compounds of the general Formula I wherein $R^1$ is $CH_2OH$ and X is O.

Medical Use

In a further aspect, the invention relates to compounds of the formula I for use in therapy, in particular for use against gastrointestinal inflammatory diseases. The invention also provides the use of a compound of the formula I in the manufacture of a medicament for the inhibition of gastric acid secretion, or for the treatment of gastrointestinal inflammatory diseases.

The compounds according to the invention may thus be used for prevention and treatment of gastrointestinal inflammatory diseases, and gastric acid-related diseases in mammals including man, such as gastritis, gastric ulcer, duodenal ulcer, reflux esophagitis and Zollinger-Ellison syndrome. Furthermore, the compounds may be used for treatment of other gastrointestinal disorders where gastric antisecretory effect is desirable, e.g. in patients with gastrinomas, and in patients with acute upper gastrointestinal bleeding. They may also be used in patients in intensive care situations, and pre- and postoperatively to prevent acid aspiration and stress ulceration.

The typical daily dose of the active substance varies within a wide range and will depend on various factors such as for example the individual requirement of each patient, the route of administration and the disease. In general, oral and parenteral dosages will be in the range of 5 to 1000 mg per day of active substance.

Pharmaceutical Formulations

In yet a further aspect, the invention relates to pharmaceutical compositions containing at least one compound of the invention, or a therapeutically acceptable salt thereof, as active ingredient.

The compounds of the invention can also be used in formulations together with other active ingredients, e.g. antibiotics such as amoxicillin.

For clinical use, the compounds of the invention are formulated into pharmaceutical formulations for oral, rectal, parenteral or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention.

Usually the amount of active compounds is between 0.1–95% by weight of the preparation, preferably between 0.1–20% by weight in preparations for parenteral use and preferably between 0.1 and 50% by weight in preparations for oral administration.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention, vegetable oil, fat, or other suitable vehicle for soft gelatin capsules. Hard gelatin capsules may contain granules of the active compound. Hard gelatin capsules may also contain the active compound in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the active substance mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.1% to 20% by weight of the active ingredient and the remainder consisting of sugar or sugar alcohols and a mixture of ethanol, water, glycerol, propylene glycol and polyethylene glycol. If desired, such liquid is preparations may contain coloring agents, flavoring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to by reconstituted with a suitable solvent extemporaneously before use.

The compounds according to the invention can also be used in formulations together with other active ingredients, e.g. for the treatment or prophylaxis of conditions involving infection by *Helicobacter pylori* of human gastric mucosa. Such other active ingredients may be antimicrobial agents, in particular:

β-lactam antibiotics such as amoxicillin, ampicillin, cephalothin, cefaclor or cefixime;

macrolides such as erythromycin, or clarithromycin;

tetracyclines such as tetracycline or doxycycline;

aminoglycosides such as gentamycin, kanamycin or amikacin;

quinolones such as norfloxacin, ciprofloxacin or enoxacin;

others such as metronidazole, nitrofurantoin or chloramphenicol; or preparations containing bismuth salts such as bismuth subcitrate, bismuth subsalicylate, bismuth subcarbonate, bismuth subnitrate or bismuth subgallate.

EXAMPLES

1. Preparation of Compounds of the Invention

Example 1.1

Synthesis of 8-(2,6-dimethylbenzylamino)-2,3,6-trimethylimidazo[1,2-a]pyridine hydrochloride

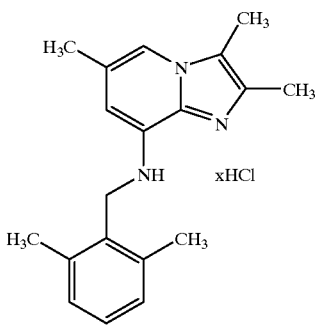

A stirred mixture of 8-amino-2,3,6-trimethylimidazo[1,2-a]pyridine (0.9 g, 5.1 mmol), zinc(II) chloride (0.84 g, 6.2 mmol) and 2,6-dimethylbenzaldehyd (0.83 g, 6.2 mmol) in methanol (50 ml) was treated with sodium cyanoborohydride (0.39 g, 6.2 mmol) and was refluxed for 3 h. The methanol was evaporated under reduced pressure and the residue was dissolved in methylene chloride and 2 M sodium hydroxide (40 ml). The organic layer was separated, dried over sodium sulfate and evaporated under reduced pressure.

The residue was purified twice by column chromatography on silica gel, using a) ethyl acetate:methylene chloride (1:2) and b) methanol:methylene chloride (1:20) as eluent. The oily product was dissolved in diethyl ether, treated with diethyl ether/HCl and the precipitated salt was filtered off to give 0.6 g (36%) of the title compound.

$^1$H-NMR (300 MHz, CDCl$_3$): δ2.33 (s, 3H), 2.38 (s, 3H), 2.45 (s, 6H), 2.50 (s, 3H), 4.40 (d, 2H), 6.40 (bs, 1H), 7.95–7.15 (m, 4H).

Example 1.2

Synthesis of 2,3-dimethyl-8-(2,6-dimethylbenzylamino)-6-fluoroimidazo[1,2-a]pyridine

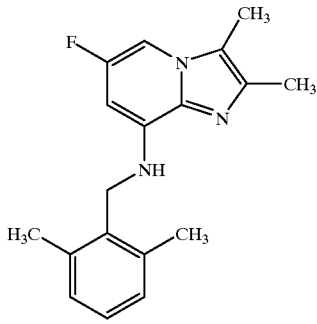

A stirred mixture of 8-amino-2,3-dimethyl-6-fluoroimidazo[1,2-a]pyridine (0.16 g, 0.89 mmol), zinc(II) chloride (0.14 g, 1.04 mmol) and 2,6-dimethylbenzaldehyd (0.14 g, 1.04 mmol) in methanol (50 ml) was treated with sodium cyanoborohydride (0.065 g, 1.04 mmol) and was refluxed for 7 h. The cooled reaction mixture was added to 0.5 M NaOH (20 ml) and the precipitated solids were filtered off and purified by column chromatography on silica gel, using methanol:methylene chloride (1:10) as eluent. Crystallization from petroleum ether gave 0.1 g (38%) of the title compound.

$^1$H-NMR (300 MHz, CDCl$_3$): δ2.30 (s, 3H), 2.34 (s, 3H), 2.40 (s, 6H) 4.35 (d, 2H), 4.95 (bs, 1H), 6.15 (dd, 1H), 7.0–7.20 (m, 4H).

Example 1.3

Synthesis of 2,3-dimethyl-8-(2,6-diethylbenzylamino)-imidazo[1,2-a]pyridine

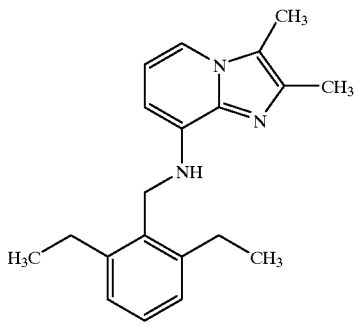

8-amino-2,3-dimethyl-imidazo[1,2-a]pyridine (0.33 g, 2.0 mmol) and 2,6-diethylbenzaldehyde (0.36 g, 2.2 mmol) were dissolved in methanol (7 ml). ZnCl$_2$ (0.30 g, 2.2 mmol) and subsequently NaBH$_3$CN (0.14 g, 2.2 mmol) in small portions were added and the mixture was refluxed under argon for 3 hours, cooled and then poured over an aqueous 1M NaOH solution (10 ml). The resultant yellow suspension was extracted with DCM (3×25 ml) and the combined organic solutions were washed with brine, dried over Na$_2$SO$_4$ and then removed. The oily residue (0.4 g) was purified by flash chromatography (DCM-EtOAc 0%–20% EtOAc) to give 0.34 g. Treatment of this oily product with hexane (2 ml) afforded 0.14 g (23%) as off-white crystals.

$^1$H-NMR (300 MHz, CDCl$_3$): δ7.2–7.3 (2H, m), 7.1 (2H, d), 6.7 (1H, t), 6.2 (1H, d), 4.8 (1H, b), 4.4 (2H, d), 2.7 (4H, q), 2.3 (6H, two singlets), 1.2 (6H, t).

Example 1.4

Synthesis of 8-(2,6-dimethylbenzyloxy)-3-hydroxymethyl-2-methylimidazo[1,2-a]pyridine

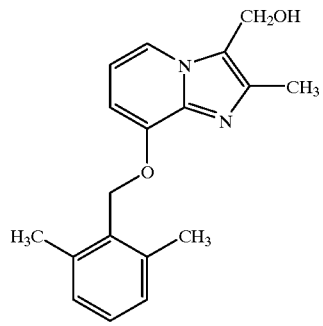

A mixture of 8-hydroxy-3-hydroxymethyl-2-methylimidazo[1,2-a]pyridine (0.89 g, 5.0 mmol), sodium carbonate (1.5 g), sodium iodide (0.4 g), 2,6-dimethylbenzylchloride (0.7 g, 4.5 mmol) and acetone (60 ml) was stirred overnight. More sodium carbonate (1.0 g) was added. The reaction mixture was refluxed for 2 h. The reaction mixture was filtered and the solvent was removed in vacuo. The residue was suspended in CH$_2$Cl$_2$/MeOH (100:5) and filtered. Vacuum evaporation of solvent gave a residue which was purified by flash chromatography eluting with CH$_2$Cl$_2$—MeOH (100:4), collecting fractions, and recrystallized from CH$_2$Cl$_2$/CH$_3$CN to give 0.37 g of the title compound.

$^1$H NMR (300 MHz, CDCl$_3$): δ7.87 (d, J=7.6 Hz, 1H), 7.15–7.08 (m, 1H), 7.0 (d, J=7.6 Hz, 2H), 6.73 (t, J=7.6 Hz, 1H), 6.63 (d, J=7.6 Hz, 1H), 5.23 (s, 2H), 4.83 (s, 2H), 2.4 (s, 6H), 2.28 (s, 3H).

Example 1.5

Synthesis of 2,3-dimethyl-8-(2,6-dimethylbenzylamino)imidazo[1,2-a]pyridine

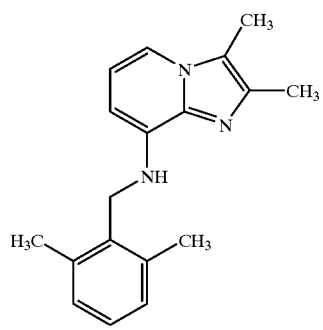

A mixture of 8-amino-2,3-dimethylimidazo[1,2-a]pyridine (0.7 g, 4.34 mmol), sodium carbonate (2.0 g), sodium iodide (0.3 g), 2,6-dimethylbenzylchloride (0.671 g, 4.34 mmol) and acetone (30 ml) was stirred overnight. The reaction mixture was filtered and the solvent was removed in vacuo. The residue was dissolved in methylene chloride and washed with aqueous NaHCO$_3$. The organic layer was separated and the solvent was evaporated. The crude product was purified by flash chromatography eluting with CH$_2$Cl$_2$/MeOH to give 0.7 g of the title compound.

$^1$H NMR (300 MHz, CDCl$_3$): δ7.25 (d, J=7.7 Hz, 1H), 7.14–7.09 (m, 1H), 7.03 (d, J=7.7 Hz, 2H), 6.73 (t, J=7.7 Hz, 1H), 6.21 (d, J=7.7 Hz, 1H), 4.79 (br "t", 1H), 4.34 (d, J=4.5 Hz, 2H), 2.38 (s, 6H), 2.34 (s, 6H).

Example 1.6

Synthesis of 2,3-dimethyl-8-(2,6-dimethylbenzyloxy)imidazo[1,2-a]pyridine

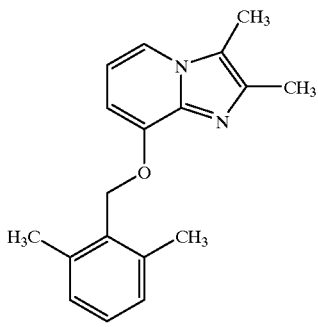

A mixture of 8-hydroxy-2,3-dimethylimidazo[1,2-a]pyridine (1.2 g, 7.41 mmol), 2,6-dimethylbenzylchloride (1.145, 7.41 mmol), sodium iodide (0.3 g), sodium carbonate (2.0 g) and acetone (50 ml) was refluxed for 3 h. After the addition of methylene chloride the reaction mixture was filtered. The solvent was removed in vacuo. The residue was dissolved in CH$_2$Cl$_2$, washed with aqueous NaHCO$_3$, dried over Na$_2$SO$_4$ and evaporated. The residue was chromatographed on silica, eluting with CH$_2$Cl$_2$—MeOH (100:5) to give 0.70 g of the desired product (from ethyl acetate-ether).

$^1$H NMR (300 MHz, CDCl$_3$): δ7.56 (d, J=6.6 Hz, 1H), 7.1 (t, J=6.6 Hz, 1H), 6.94–6.85 (m, 3H), 6.73 (d, J=6.6 Hz, 1H), 2.31 (s, 3H), 2.26 (s, 3H), 2.24 (s, 6H).

Example 1.7

Synthesis of 2,3-dimethyl-8-(2-ethyl-6-methylbenzylamino)imidazo[1,2-a]pyridine

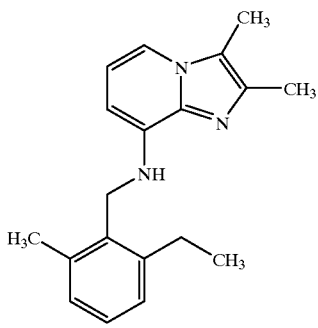

8-Amino-2,3-dimethylimidazo[1,2-a]pyridine (0.3 g, 1.86 mmol) and 2-ethyl-6-methylbenzylchloride (0.31 g, 1.84 mmol) were dissolved in 5 ml dimethoxyethane. Potassium iodide (0.2 g, 1.2 mmol) and Na$_2$CO$_3$ (0.3 g, 2.8 mmol) were added and the mixture was refluxed for 4 hours. The solvent was evaporated and the residue was purified by column chromatography on silica gel using a mixture of methylene chloride and ethyl acetate (60:40) as eluent. 230 mg (42%) of the title compound was obtained.

$^1$H-NMR (300 MHz, CDCl$_3$): δ1.22 (t, 3H), 2.35 (s, 6H), 2.39 (s, 3H), 2.70 (q, 2H), 4.35 (d, 2H), 4.81 (t, 1H), 6.21 (d, 1H), 6.73 (t, 1H), 7.01–7.10 (m, 2H), 7.13–7.19 (m, 1H), 7.24 (d, 1H).

Example 1.8

Synthesis of 6-bromo-2,3-dimethyl-8-(2,6-dimethylbenzylamino)imidazo[1,2-a]pyridine

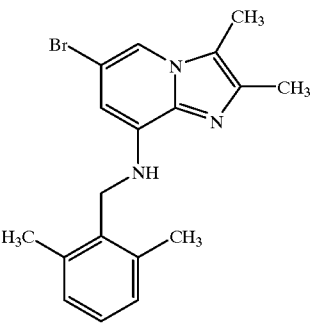

A mixture of 8-amino-6-bromo-2,3-dimethylimidazo[1,2-a]pyridine (1.2 g, 5.0 mmol), 2,6-dimethylbenzylchloride (0.772 g, 5.0 mmol), sodium carbonate (0.8 g), sodium iodide (0.2 g) and acetone (45 ml) was stirred overnight. More 2,3-dimethylbenzylchloride (0.285 g) was added and the reaction mixture was refluxed for 5 h. After addition of acetone the reaction mixture was filtered. The solvent was removed in vacuo and the residue was dissolved in CH$_2$Cl$_2$, washed with NaHCO$_3$, dried over Na$_2$SO$_4$ and evaporated. The crude product dissolved in ethyl acetate and petroleum ether was added. Filtration and evaporation of the solvent gave a residue which was recrystallized from ethyl acetate to give 1.45 g of the title compound.

$^1$H NMR (300 MHz, CDCl$_3$): δ7.37 (d, J=1.5 Hz, 1H), 7.15–7.09 (m, 1H), 7.04 (d, J=7.5 Hz, 2H), 6.28 (d, J=1.5 Hz, 1H), 4.88 ("t", 1H). 4.33 (d, J=4.13 Hz, 2H), 2.38 (s, 6H), 2.3 (s, 3H), 2.29 (s, 3H).

Example 1.9

Synthesis of 8-(2,6-dimethylbenzylamino)-3-hydroxymethyl-2-methylimidazo[1,2-a]pyridine

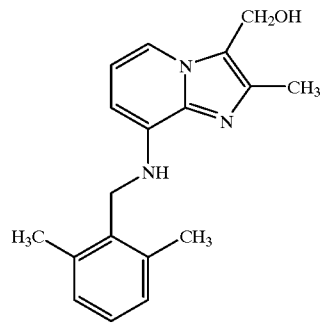

A solution of vitride (40 ml, 136 mmol) in toluene (25 ml) was added dropwise to a nitrogen-purged solution of 3-carboethoxy-8-(dimethylbenzylamino)-2-methylimidazo[1,2-a]pyridine (8.0 g, 23.71 mmol) in toluene (100 ml). The ice-bath was removed and the reaction mixture was stirred at room temperature for 105 min. The reaction mixture was cooled to 0° C. and quenched by addition of water (36 ml). The mixture was filtered and the organic layer washed with aqueous NaHCO$_3$, dried over Na$_2$SO$_4$ and concentrated. Acetonitrile (20 ml) was added and the product was collected by filtration. The crystalline product was washed twice with acetonitrile and dried in vacuo. Yield 5.6 g.

$^1$H NMR (300 MHz, CDCl$_3$): δ7.58 (d, J=7.1 Hz, 1H), 7.15–7.1 (m, 1H), 7.05 (d, J=7.1 Hz, 2H), 6.74 (t, J=7.1 Hz, 1H), 6.28 (d, J=7.1 Hz, 1H), 4.84 (br t, J=4.5 Hz, 1H), 4.8 (s, 2H), 4.35 (d, J=4.5 Hz, 2H), 2.4 (s, 6H), 2.2 (s, 3H).

Example 1.10

Synthesis of 6-chloro-2,3-dimethyl-8-(2,6-dimethylbenzylamino)imidazo[1,2-a]pyridine

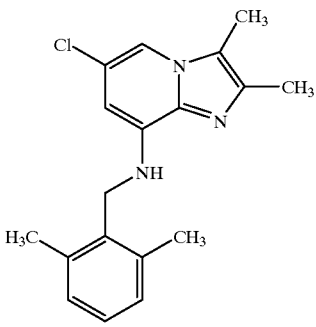

A mixture of 8-amino-6-chloro-2,3-dimethylimidazo[1,2-a]pyridine (0.894 g, 4.57 mmol), 2,6-dimethylbenzaldehyde (0.77 g, 5.7 mmol), ZnCl$_2$ (1.08 g, 7.92 mmol), NaB(CN)H$_3$ (0.36 g, 5.7 mmol) and MeOH (35 ml) was refluxed for 3.5 h. More 2,6-dimethylbenzaldehyde (0.25 g in 4 ml MeOH), ZnCl$_2$ (0.55 g) and NaB(CN)H$_3$ (0.35 g) were added. The reaction mixture was refluxed for additional 4 h. Subsequent workup by addition of 1 M NaOH (150 ml), and water (50 ml), followed by extraction of the mixture with CH$_2$Cl$_2$, drying, and evaporation of solvent gave a solid residue. The crude product dissolved in ethyl acetate and ether was added. Filtration and evaporation of solvent gave a residue which was recrystallized from ethyl acetate to give 0.52 g product.

$^1$H NMR (300 MHz, CDCl$_3$): δ7.28 (d, J=1.7 Hz, 1H), 7.15–7.1 (m, 1H), 7.04 (d, J=12 Hz, 2H), 6.2 (d, J=1.7 Hz, 1H), 4.89 (br "t", 1H), 4.33 (d, J=4 Hz, 2H), 2.37 (s, 6H), 2.33 (s, 3H), 2.32 (s, 3H).

Example 1.11

Synthesis of 2,3-dimethyl-8-(2,6-dimethyl-4-fluorobenzylamino)imidazo[1,2-a]pyridine

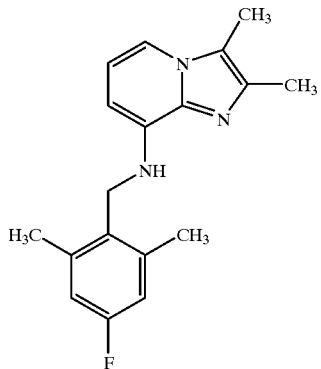

8-Amino-2,3-dimethylimidazo[1,2-a]pyridine (0.5 g, 3.1 mmol) was dissolved in acetonitrile (6 ml). To the solution were added 2,6-dimethyl-4-fluoro-benzylbromide (0.67 g, 3.1 mmol) and potassium carbonate (0.47 g, 3.4 mmol). The mixture was refluxed for 16 h. Methylene chloride (12 ml) and a sodium chloride solution (20 ml) was added. The organic layer was separated, dried over sodium sulfate and evaporated under reduced pressure. The crude product was purified by chromatography (ethyl acetate:petroleum-ether 1:1). 400 mg of the title compound was obtained as a solid.

$^1$-NMR (300 MHz, CDCl$_3$): δ2.3 (s, 6H), 2.3 (s,6H), 4.2 (d,2H), 4.65 (b,1H), 6.15 (d, 1H), 6.65–6.75 (m,3H), 7.2 (d,1H)

Example 1.12

Synthesis of 2,6-dimethyl-8-(2,6-dimethylbenzylamino)-3-hydroxymethyl imidazo[1,2-a]pyridine

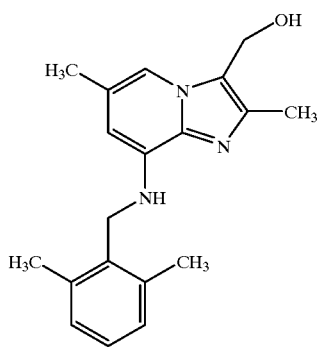

A solution of 3-carboethoxy-2,6-dimethyl-8-(2,6-dimethylbenzylamino)imidazo[1,2-a]pyridine (0.4 g, 1.1 mmol) in 10 ml toluene was cold with ice- water, Red-AL 65% in to toluene (2.1 g, 6.6 mmol) was added after 30 min. The solution was stirred for 2 h at room temperature. 10 ml of Rochelle-salt solution (sodium potassium tartrate tetrahydrate, 35 g/250 ml water) was added dropwise, 10 ml toluene was added, the organic layer was separated and washed with water, dried over sodium sulfate and evaporated under reduced pressure. The residue was purified by column chromatography on silica gel, eluent dichloromethane:methanol 9:1, to give 0.21 g, (62%) of the title compound.

¹H-NMR (300 MHz, CDCl₃): δ1.65 (s, 1H), 2.30 (d, 6H), 2.38 (s, 6H), 4.37 (d, 2H), 4.75 (s, 1H), 4.85 (s, 2H), 6.15 (s, 1H), 7.0–7.15 (m, 3H), 7.40 (s, 1H).

Example 1.13

Synthesis of 2,6-dimethyl-8-(2,6-dimethyl-4-fluorobenzylamino)-3-hydroxymethylimidazo[1,2-a]pyridine

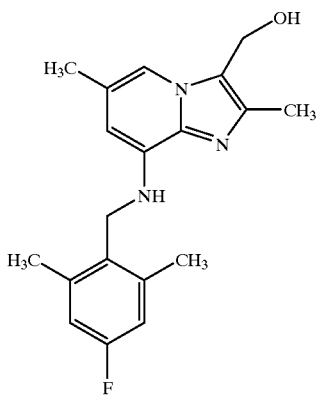

A solution of 0.4 g (1.1 mmol) of 3-carboethoxy-2,6-dimethyl-8-(2,6-dimethyl-4-fluorobenzylamino)-imidazo[1,2-a]pyridine in 10 ml toluene was chilled with ice-water, (2.1 g, 6.6 mmol). Red-l 65% in toluene was added after 30 min. The solution was stirred for 2 h at room temperature. 10 ml of Rochelle-salt solution, (35 g sodium potassium tartrate tetrahydrate/250 ml water) was added dropwise, 10 ml toluene was added, the organic layer was separated, washed with water, dried over sodium sulfate and evaporated under reduced pressure.

The residue was purified by column chromatography on silica gel, eluent dichloromethane: methanol 95:5, to give 0.3 g (83%) of the title copound.

¹H NMR (300 MHz, CDCl₃): δ2.26 (s, 3H), 2.33 (s, 3H), 2.37 (s, 6H), 4.28 (d, 2H), 4.70 (s, 1H), 4.82 (s, 2H), 6.14 (s, 1H), 6.75 (d, 2H), 7.42 (s, 1H).

Example 1.14

Synthesis of 8-(2,6-dimethyl-4-fluorobenzylamino)-2,3,6-trimethylimidazo[1,2-a]pyridine hydrochloride

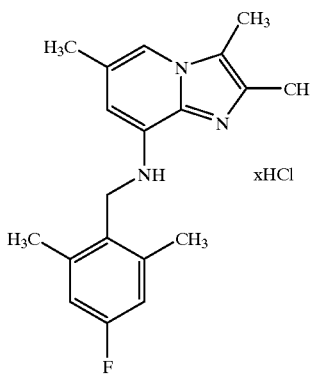

A stirred mixture of 8-amino-2,3,6-trimethylimidazo[1,2-a]pyridine (0.5 g, 2.85 mmol), 2,6-dimethyl-4-fluorobenzylbromide (0.7 g, 3.4 mmol), potassium carbonate (0.6 g, 4.6 mmol), sodium iodide (0.1 g), 15 ml acetonitrile was refluxed over night. The solvent was evaporated under reduced pressure and the residue was dissolved in dichloromethane and washed with water. The organic layer was dried over sodium sulfate and evaporated under reduced pressure. The residue was purified by column chromatography on silica gel eluent hexane:ethyl acetate 2:1. The oil product was dissolved in diethyl ether, treated with is diethyl ether/HCl and the precipitated salt was filtered off to give 0.55 g, (56%) of the title compound.

¹H NMR (300 MHz, CDCl₃): δ2.22 (s, 3H), 2.30 (d, 12H), 4.23 (d, 2H), 4.68 (s, 1H), 6.05 (s, 1H), 6.70 (d, 2H), 7.00 (s, 1H).

Example 1.15

Synthesis of 2,3-dimethyl-8-(2,6-dimethyl-4-chlorobenzylamino)imidazo[1,2-a]pyridine

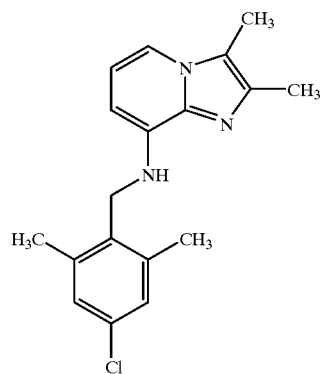

A mixture of 4-chloro-2,6-dimethylbenzylbromide and 2-chloro-4,6-dimethylbenzylbromide (1.1 g, 4.68 mmol) and 8-amino-2,3-dimethylimidazo[1,2-a]pyridine (4.65 mmol) was dissolved in 15 ml dimethoxyethane. Potassium iodide (0.5 g, 3.0 mmol) and Na₂CO₃ (1 g, 9.4 mmol) was added. The mixture was refluxed for 4 hours. The solvent was evaporated and the residue was purified by column chromatography on silica gel. The product was eluted with a mixture of methylene chloride and ethyl acetate (70:30). 70 mg of the title compound was obtained.

¹H-NMR (300 MHz, CDCl₃): δ2.35 (s, 6H), 4.29 (d, 2H), 4.74 (t, 1H), 6.19 (d, 1H), 6.72 (t, 1H), 7.04 (s, 2H), 7.25 (d, 1H).

Example 1.16

Synthesis of 2,6-dimethyl-8-(2-ethyl-6-methylbenzylamino)-3-hydroxymethylimidazo[1,2-a]pyridine

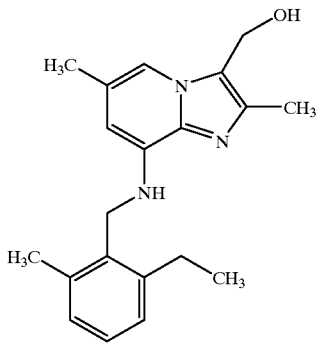

3-Carboethoxy-2,6-dimethyl-8-(2-ethyl-6-methylbenzylamino)imidazo[1,2-a]pyridine (1.0 g 2.8 mmol) was added to tetrahydrofuran (25 ml) and was stirred at +5° C. Lithium aluminum hydride (0.5 g, 13 mmol) was added in portions during 1.5 h so that the temperature remained below +10° C. After stirring the mixture at room temperature for an additional 1 h, 0.5 ml of water was added dropwise, followed by 0.5 ml of 15% sodium hydroxide and then 1.5 ml of water. The solids were removed by filtration and washed thoroughly with tetrahydrofuran and methylene chloride. The filtrate and washings were combined and dried and the solvents were removed under reduced pressure. The residue was solved in methylene chloride and washed with water. The organic layer was separated, dried over sodium sulfate, evaporated under reduced pressure and the residue was purified by column chromatography on silica gel using ethylacetate:methylene chloride (1:1) as eluent. Crystallization from petroleum ether:diethyl ether (1:1) gave 0.37 g (41%) of the title compound.

$^1$H-NMR (300 MHz, CDCl$_3$): δ1.25 (t, 3H), 2.25 (s, 3H), 2.35 (s, 3H), 2.40 (s, 3H), 2.70 (q, 2H), 4.35 (d, 2H), 4.75 (bs, 1H), 4.80 (s 2H), 6.15 (s, 1H), 7.05–7.25 (m, 3H), 7.40 (s, 1H).

Example 1.17

Synthesis of 8-(2,6-diethylbenzylamino)-2,6-dimethyl-3-hydroxymethyl imidazo[1,2-a]pyridine

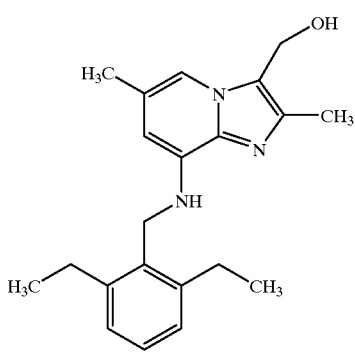

A solution of 3-carboethoxy-2,6-dimethyl-8-(2,6-diethylbenzylamino)imidazo[1,2-a]pyridine (1.75 g, 4.6 mmol) in 30 ml tetrahydrofuran was treated with lithium aluminiumhydride (0.7 g, 18.5 mmol) at room temperature during 3.5 h. The reaction was complete after 4 h and was quenched carefully by dropwise addition of water (0.7 ml), aqueous sodium hydroxide (0.7 ml, 15%) and again water (2 ml). The mixture was extracted with chloroform and the organic layer was concentrated. The residue was recrystallized in ethanol and the white crystalline product was filtrated, washed with diethyl ether and dried in vacuo, which gave 1.5 g (96%) yield.

$^1$H-NMR (500 MHz, CDCl$_3$): δ1.23 (t, 6H), 1.99 (s, 1H), 2.25 (s, 3H), 2.33 (s, 3H), 2.73 (q, 4H), 4.34 (d, 2H), 4.80 (s, 3H), 6.13 (s, 1H), 7.09 (d, 2H), 7.22 (t, 1H), 7.40 (s, 1H).

Example 1.18

Synthesis of 8-(2,6-diethylbenzylamino) 2,3,6-trimethylimidazo[1,2-a]pyridine

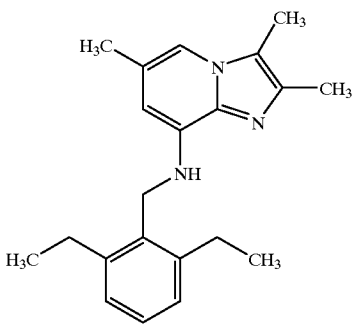

A stirred mixture of 8-amino-2,3,6-trimethylimidazo[1,2-a]pyridine (0.5 g, 2.8 mmol), 2,6-diethylbenzaldehyde (0.7 g, 4.3 mmol) and zinc(II)chloride (0.44 g, 3 mmol) in 50 ml methanol was treated with sodium cyanoborohydride (0.19 g, 3 mmol) and then refluxed for 20 h. The methanol was evaporated under reduced pressure and the residue was dissolved in dichloromethylene and water. The organic layer was separated, dried over sodium sulfate and evaporated under reduced pressure. The residue was chromatographed on silica gel with dichloromethylene first and then dichloromethylene:ethylacetate (1:1) which yielded 0.42 g of the title compound.

$^1$H-NMR (300 MHz, CDCl$_3$): δ1.25 (t, 6H), 2.28 (s, 3H), 2.30 (s, 3H), 2.33 (s, 3H), 2.71 (q, 4H), 4.36 (d, 2H), 4.84 (s, 1H), 6.10 (s, 1H), 7.04–7.23 (m, 4H)

Example 1.19

Synthesis of 8-(2-ethyl-6-methylbenzylamino)-2,3,6-trimethylimidazo[1,2-a]pyridine

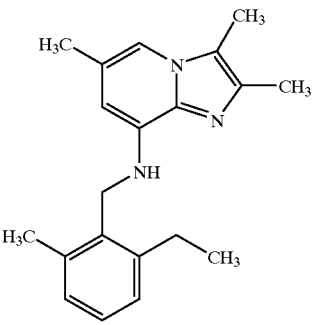

A stirred mixture of 8-amino-2,3,6-trimethylimidazo[1,2-a]pyridine (0.5 g, 2.8 mmol), 2-ethyl-6-methylbenzaldehyde (0.45 g, 3 mmol) and zinc(II)chloride (0.4 g, 3 mmol) in 50 ml methanol was treated with sodium cyanoborohydride (0.19 g, 3 mmol) and refluxed for 20 h. The methanol was evaporated under reduced pressure and the residue was dissolved in dichloromethylene and water. The organic layer was separated, dried over sodium sulfate and evaporated under reduced pressure. The residue was chromatographed on silicagel with dichloromethylene:methanol (10:1) which yielded 0.28 g (33%) of the title compound.

$^1$H-NMR (300 MHz, CDCl$_3$): δ1.22 (t, 3H), 2.32 (s, 6H), 2,34 (s, 3H), 2.38 (s, 3H), 2.72 (q, 2H), 4.33 (d, 2H), 4.77 (s, 1H), 6.08 (s, 1H), 7.03–7.19 (m, 4H).

Example 1.20

Synthesis of 8-(2,6-dimethyl-4-fluorobenzyloxy)-3-hydroxymethyl-2-methylimidazo[1,2a]pyridine

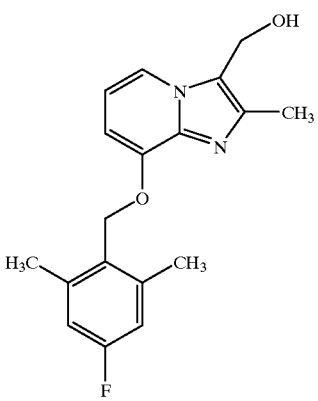

Lithium aluminum hydride (0.31 g 8.4 mmol) was added to tetrahydrofuran (30 ml) and 3-carboethoxy-8-(2,6-dimethyl-4-fluorobenzyloxy)-2-methylimidazol[1,2-a]pyridine (1.5 g 4.2 mmol) solved in tetrahydrofuran (30 ml) was added dropwise during 30 min. 0.31 ml of water was added dropwise, followed by 0.31 ml of 15% sodium hydroxide and then 0.93 ml of water. The solids were removed by filtration and washed thoroughly with methanol:methylene chloride (1:1). The filtrate and washings were combined and the solvents were removed under reduced pressure. The residue was purified by column chromatography on silica gel using methylene chloride:methanol (9:1) as eluent. Treating the residue with acetonitrile gave 0.9 g (69%) of the title compound.

$^1$H-NMR (300 MHz, DMSO-d$_6$): δ2.25 (s, 3H), 2.35 (s, 6H), 4.85 (d, 2H), 5.1 (t, 1H), 5.2 (s, 2H), 6.8–7.05 (m, 4H), 7.95 (d, 1H)

Example 1.21

Synthesis of 6-bromo-8-(2,6-dimethyl-4-fluorobenzylamino)-3-hydroxymethyl-2-methylimidazo[1,2-a]pyridine

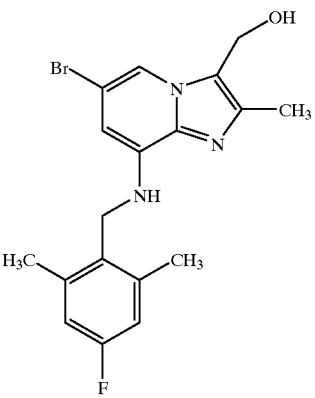

LiBH$_4$ (70 mg) was added in portions and during 4 h to a refluxed solution of 6-bromo-3-carboethoxy-8-(2,6-dimethyl-4-fluorobenzylamino)-2-methylimidazo[1,2-a]pyridine (100 mg, 0.23 mmol) in THF. The reaction mixture was quenched by addition of diluted HCl and methylene chloride was added. The organic layer was separated, dried and evaporated in vacuo. The residue was purified by column chromatography on silica gel, using methylene chloride:ethyl acetate (100:10) as eluent to give 40 mg (44%) of the title compound.

$^1$H-NMR (300, MHz, CDCl$_3$): δ7.72 (s, 1h), 6.75 (d, 2h), 6.35 (s, h), 4.9 (t, 1h), 4.8 (s, 2h), 4.3 (d, 2h), 2.35 (s, 6h), 2.25 (s, 3h).

Example 1.22

Synthesis of 2,6-dimethyl-8-(2,6-dimethylbenzyloxy)-3-hydroxymethylimidazo[1,2-a]pyridine

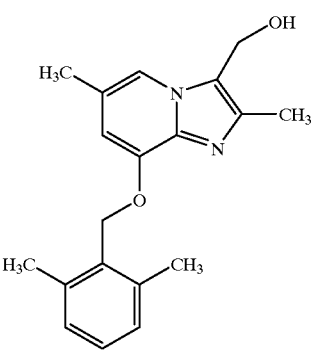

A mixture of vitride (3 ml, 10.2 mmol) in toluene (3 ml) was added dropwise to nitrogene-purged solution of 3-carboethoxy-2,6-dimethyl-8-(2,6-dimethylbenzyloxy) imidazo[1,2-a]pyridine (0.68 g, 1.93 mmol) in toluene (15 ml). The ice-bath was removed and the reaction mixture was stirred at room temp. For 2 h and 15 min. The reaction mixture was cooled to 0° C. and quenched by addition of water (6 ml). Methylene chloride/methanol was added and the reaction mixture was filtered. The solvent was removed in vacuo and the residue was purified by column chromatography on silica gel, using methylene chloride:methanol (100:5) as eluent to give 0.35 g (58%) of the title compound.

$^1$H-NMR (300, MHz, CDCl$_3$): δ7.65 (s, 1H), 7.10 (t, 1H), 7.0 (d, 2H), 6.50 (s, 1H), 5.2 (s, 2H), 4.8 (s, 2H), 2.4 (s, 6H), 2.35 (s, 3H), 2.25 (s, 3H).

Example 1.23

Synthesis of 8-(2,6-dimethyl-4-fluorobenzylamino)-3-hydroxymethyl-2-methylimidazo[1,2-a]pyridine

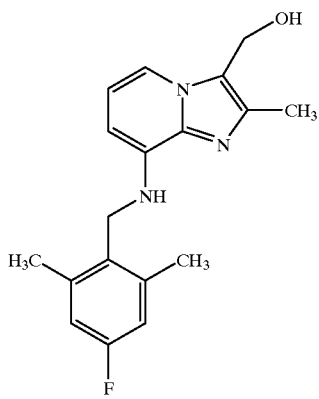

A solution of 0.6 g (1.7 mmol) of 3-carboethoxy-8-(2,6-dimethyl-4-fluorobenzylamino)-2-methylimidazo[1,2-a] pyridine in 30 ml toluene was cold with ice-water. Red-l 65% 2.1 g (6.6 mmol) in toluene was added during 30 min. The solution was stirred 1 h at rt. 25 ml of Rochelle-salt solution, (35 g sodium potassium tartrate tetrahydrate/250 ml water) was added dropwise and the organic layer was separated. The water layer was washed with methylene chloride which was separated. The combined organic solvents were dried over sodium sulfate and evaporated under reduced pressure. The residue was purified by column chromatography on silica gel, eluent dichloromethane:methanol 95:5, to give 0.42 g, (79%) of the title compound.

$^1$H-NMR (300, MHz, CDCl$_3$): δ2.15 (s, 3H), 2.35 (s, 6H), 4.30 (d, 2H), 4.75 (s, 2H), 4.85 (t, 1H), 6.25 (d, 1H), 6.70–6.80 (m, 3H), 7.55 (d, 1H).

Example 1.24

Synthesis of 2,6-dimethyl-8-(2-ethyl-4-fluoro-6-methylbenzylamino)-3-hydroxymethylimidazo[1,2-a]pyridine

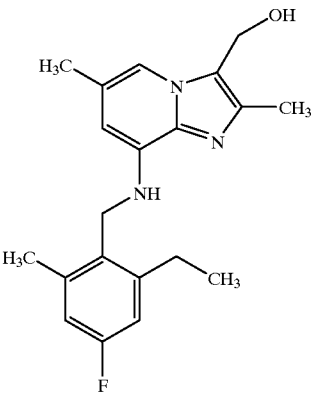

To a mixture of LiAlH$_4$ (0.08 g, 2.1 mmol) in tetrahydrofuran (15 ml) was added 3-carboethoxy-2,6-dimethyl-8-(2-ethyl-4-fluoro-6-methylbenzylamino)imidazo[1,2-a] pyridine (0.4g, 1.0) mmol in tetrahydrofuran (15 ml). After stirring the mixture at room temperature for 4 h., 0.1 ml of water was added dropwise, followed by 0.1 ml of 15% sodium hydroxide and then 0.3 ml of water. The solids were removed by filtration and washed thoroughly with tetrahydrofuran. The filtrate and washings were combined and dried and the solvent was removed under reduced pressure. The residue was purified by column chromatography on silica gel using methylene chloride:methanol (9:1) as eluent. Crystallization from acetonitril gave 0.32 g (89%) of the title compound.

$^1$H-NMR (300 MHz, CDCl$_3$): δ1.2 (t, 3H), 2.2 (s, 3H), 2.35 (s, 3H), 2.4 (s, 3H), 2.75 (q, 2H), 4.3 (d, 2H), 4.75 (bs, 3H), 6.15 (s, 1H), 6.75–6.85 (m, 2H), 7.45 (s, 1H).

Example 1.25

Synthesis of 8-(2-ethyl-4-fluoro-6-methylbenzylamino)-2,3,6-trimethyl imidazo[1,2-a] pyridine

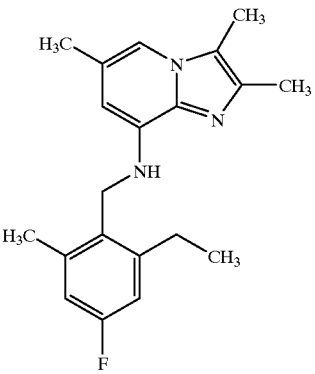

8-Amino-2,3,6-trimethylimidazo[1,2-a]pyridine (0.38 g, 2.16 mmol) and 2-ethyl-4-fluoro-6-methylbenzylbromide (0.50 g, 2.16 mmol) were dissolved in 10 ml dimethoxyethane. Potassium iodide (0.2 g, 1.2 mmol) and Na$_2$CO$_3$ (0.4 g, 3.8 mmol) were added and the mixture was refluxed for 6 hours. The solvent was evaporated and the residue was purified by column chromatography on silica gel using a mixture of methylene chloride and ethyl acetate (60:40) as eluent. 203 mg (29%) of the title compound was obtained.

$^1$H-NMR (300 MHz, CDCl$_3$): δ1.21 (t, 3H), 2.32 (s, 6H), 2.33 (s, 3H), 2.37 (s, 3H), 2.71 (q, 2H), 4.28 (d, 2H), 4.68 (t, 1H), 6.06 (s, 1H), 6.73–6.80 (m, 2H), 7.05 (s, 1H).

Example 1.26

Synthesis of 2,3-dimethyl-8-(2,6-dimethyl-4-fluorobenzyloxy)imidazo[1,2-a]pyridine

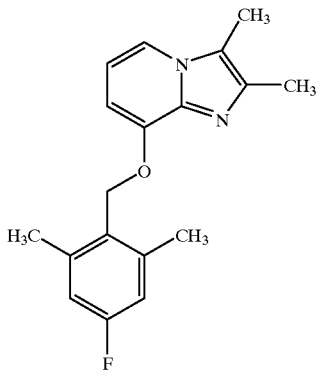

2,3-Dimethyl-8-hydroxyimidazo[1,2-a]pyridine (1.7 g, 10 mmol), 2,6-dimethyl-4-fluorobenzylbromide (2.3 g, 10 mmol), sodium iodide (0.5 g, 0.3 mmol) and sodium carbonate (2.6 g, 28 mmol) were added to acetone (75 ml) and the mixture was refluxed for 6 h. Methylene chloride was added and the mixture was filtered and the solvents were evaporated under reduced pressure. Purification by column chromatography on silica gel using methylene chloride:ethylacetate(1:2) as eluent gave the title compound as a white powder. (0.85 g, 28%)

$^1$H-NMR (300 MHz, CDCl$_3$): δ2.36 (s, 3H), 2.38 (s, 9H), 5.15 (s, 2H), 6.57 (d, 1H), 6.68–6.75 (m, 3H), 7.46, (d, 1H).

Example 1.27

Synthesis of 2,3-dimethyl-8-(2-ethyl-6-methylbenzyloxy)imidazo[1,2-a]pyridine

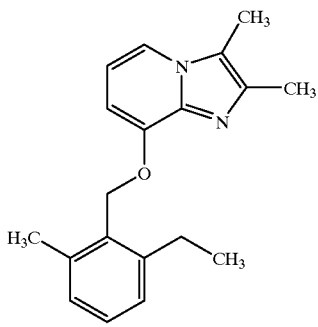

2,3-Dimethyl-8-hydroxyimidazo[1,2-a]pyridine (0.8 g, 5 mmol), 2-ethyl-6-methylbenzyl chloride, sodium iodide (0.25 g, 1.7 mmol) and sodium carbonate (1.2 g, 11 mmol) were added to acetone (40 ml) and the mixture was refluxed for 5 h. The acetone was evaporated and the residue was solved in methylene chloride and washed with water. The organic solvent was dried and was evaporated under reduced pressure. The residue was purified twice by column chromatography on silica gel using (a) methylene chloride:ethylacetate(1:2), (b) methylene chloride:ethylacetate(2:1), as eluent to give the title compound. (0.02 g, 1.4%)

$^1$H-NMR (300 MHz, CDCl$_3$): δ1.2 (t, 3H), 2.36 (s, 3H), 2.38 (s, 3H), 2.40 (s, 3H), 2.74 (q, 2H), 5.21 (s, 2H), 6.59 (d, 1H), 6.7 (t, 1H), 7.04 (m, 2H), 7.17 (t, 1H), 7.45 (d, 1H).

Example 1.28

Synthesis of 8-(2-ethyl-6-methylbenzyloxy)-3-hydroxymethyl-2-methylimidazo[1,2-a]pyridine

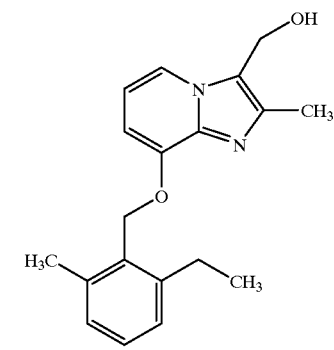

To a mixture of LiAlH$_4$ (0.08 g, 2.1 mmol) in tetrahydrofuran (25 ml) was added 3-carboethoxy-8-(2-ethyl-6-methylbenzyloxy)-2-methylimidazo[1,2-a]pyridine (1.0 g, 2.8 mmol) in tetrahydrofuran (25 ml). After stirring the mixture at room temperature for 2 h., 0.2 ml of water was added dropwise, followed by 0.2 ml of 15% sodium hydroxide and then 0.6 ml of water. The solids were removed by filtration and the solvent was removed under reduced pressure. The residue was purified by column chromatography on silica gel using methylene chloride:methanol (9:1) as eluent. Crystallization from diethyl ether gave 0.52 g (60%) of the title compound.

$^1$ H-NMR (300 MHz, CDCl$_3$): δ1.2 (t, 3H), 2.25 (s, 3H), 2.4 (s, 3H), 2.75 (q, 2H), 4.75 (s, 2H), 5.2 (s, 2H), 6.65–6.75 (m, 2H), 7.0–7.2 (m, 3H), 7.85 (d, 1H).

TABLE 1

Summary of the compounds according to Examples 1.1 to 1.28

| Example | R$^1$ | R$^2$ | R$^3$ | R$^4$ | R$^5$ | X |
|---|---|---|---|---|---|---|
| 1.1 | CH$_3$ | CH$_3$ | CH$_3$ | H | CH$_3$ | NH |
| 1.2 | CH$_3$ | CH$_3$ | CH$_3$ | H | F | NH |
| 1.3 | CH$_3$ | CH$_2$CH$_3$ | CH$_2$CH$_3$ | H | H | NH |
| 1.4 | CH$_2$OH | CH$_3$ | CH$_3$ | H | H | O |
| 1.5 | CH$_3$ | CH$_3$ | CH$_3$ | H | H | NH |
| 1.6 | CH$_3$ | CH$_3$ | CH$_3$ | H | H | O |
| 1.7 | CH$_3$ | CH$_3$ | CH$_2$CH$_3$ | H | H | NH |
| 1.8 | CH$_3$ | CH$_3$ | CH$_3$ | H | Br | NH |
| 1.9 | CH$_2$OH | CH$_3$ | CH$_3$ | H | H | NH |
| 1.10 | CH$_3$ | CH$_3$ | CH$_3$ | H | Cl | NH |
| 1.11 | CH$_3$ | CH$_3$ | CH$_3$ | F | H | NH |
| 1.12 | CH$_2$OH | CH$_3$ | CH$_3$ | H | CH$_3$ | NH |
| 1.13 | CH$_2$OH | CH$_3$ | CH$_3$ | F | CH$_3$ | NH |
| 1.14 | CH$_3$ | CH$_3$ | CH$_3$ | F | CH$_3$ | NH |
| 1.15 | CH$_3$ | CH$_3$ | CH$_3$ | Cl | H | NH |
| 1.16 | CH$_2$OH | CH$_3$ | CH$_2$CH$_3$ | H | CH$_3$ | NH |
| 1.17 | CH$_2$OH | CH$_2$CH$_3$ | CH$_2$CH$_3$ | H | CH$_3$ | NH |
| 1.18 | CH$_3$ | CH$_2$CH$_3$ | CH$_2$CH$_3$ | H | CH$_3$ | NH |

TABLE 1-continued

Summary of the compounds according to Examples 1.1 to 1.28

| Example | R$^1$ | R$^2$ | R$^3$ | R$^4$ | R$^5$ | X |
|---|---|---|---|---|---|---|
| 1.19 | CH$_3$ | CH$_3$ | CH$_2$CH$_3$ | H | CH$_3$ | NH |
| 1.20 | CH$_2$OH | CH$_3$ | CH$_3$ | F | H | O |
| 1.21 | CH$_2$OH | CH$_3$ | CH$_3$ | F | Br | NH |
| 1.22 | CH$_2$OH | CH$_3$ | CH$_3$ | H | CH$_3$ | O |
| 1.23 | CH$_2$OH | CH$_3$ | CH$_3$ | F | H | NH |
| 1.24 | CH$_2$OH | CH$_3$ | CH$_2$CH$_3$ | F | CH$_3$ | NH |
| 1.25 | CH$_3$ | CH$_3$ | CH$_2$CH$_3$ | F | CH$_3$ | NH |
| 1.26 | CH$_3$ | CH$_3$ | CH$_3$ | F | H | O |
| 1.27 | CH$_3$ | CH$_3$ | CH$_2$CH$_3$ | H | H | O |
| 1.28 | CH$_2$OH | CH$_3$ | CH$_2$CH$_3$ | H | H | O |

Preparation of Intermediates

Example 2.1

Synthesis of 2,6-dimethyl-4-fluorobenzylbromide

A mixture of 3,5-dimethyl-fluorobenzene (5 g, 0.04 mol), paraformaldehyde (15 g), hydrobromic acid (70 ml) (30% in acetic acid) and acetic acid (25 ml) was stirred at ambient temperature for 4.5 h. To the mixture were water and petroleum ether added and the organic layer was separated dried over anhydrous sodium sulfate and evaporated carefully under reduced pressure. The residue was purified by column chromatography on silica gel with petroleum ether as eluent to give the desired product. (3.7 g, 43%)

$^1$H-NMR (300 MHz, CDCl$_3$): δ2.5 (s, 6H), 4.55 (s, 2H), 6.75 (d, 2H)

Example 2.2

Synthesis of 2-ethyl-6-methylbenzylchloride

2-Ethyl-6-methylbenzylalkohol (1.0 g, 6.67 mmol) was dissolved in 10 ml methylene chloride. Thionyl chloride (1.0 g, 8.5 mmol) was added. The mixture was stirred over night at ambient temperature. The reaction mixture was evaporated. The residue was dissolved in ethylene chloride and filtered through 5 g of silica gel. The filtrate was evaporated. 1.0 g (89%) of the title compound (oil) was obtained.

$^1$H-NMR (300 MHz, CDCl$_3$): δ1.29 (t, 3H), 2.46 (s, 3H), 2.76 (q, 2H), 4.71 (s, 2H), 7.02–7.2 (m, 3H).

Example 2.3

Synthesis of 8-amino-2,3,6-trimethylimidazo[1,2-a]pyridine

To a solution of 2,3-diamino-5-methylpyridine (2.0 g, 16 mmol) in ethanol (100 ml) was added 3-bromo-2-butanon (2.4 g, 16 mmol). The reaction mixture was refluxed for 16 h. An additional amount of 3-bromo-2-butanon (1.0 g 6.7 mmol) and triethylamine (1.0 g, 9.9 mmol) were added and the mixture was refluxed for 2 h. The ethanol was evaporated under reduced pressure and the residue was treated with methylene chloride and a solution of bicarbonate. The organic layer was separated, dried over sodium sulfate and evaporated under reduced pressure. The oily residue was purified by column chromatography on silica gel, using methanol:methylene chloride (1:20) as eluent to give the desired product (1.05 g, 37%).

$^1$H-NMR (300 MHz, DMSO-d$_6$): δ2.15 (s, 3H), 2.25 (s, 3H), 2.3 (s, 3H), 5.45 (bs, 2H), 6.05 (s, 1H), 7.20 (s, 1H).

Example 2.4

Synthesis of 2-amino-5-fluoro-3-nitropyridine

To a solution of 2-amino-5-fluoropyridine (8.6 g, 77 mmol) in conc. sulfuric acid (40 ml) was added dropwise (30 min) fuming nitric acid (3.25 ml, 77 mmol) at a temperature of +3° C. The reaction mixture was stirred at room temperature for 1 h and at +55° C. for 1 h. The mixture was poured onto ice and neutralized with 10 M sodium hydroxide and was extracted with methylene chloride. The organic layer was separated, dried over sodium sulfate and evaporated under reduced pressure. The residue was purified twice by column chromatography on silica gel, using (i) methanol:methylene chloride (1:20) and (ii) diethyl ether:petroleum ether (1:1) as eluent to give the title compound (0.44 g, 3.6%).

$^1$H-NMR (300 MHz, CDCl$_3$): δ6.65 (bs, 2H), 8.20 (dd, 1H), 8.35 (d, 1H)

Example 2.5

Synthesis of 2,3-diamino-5-fluoropyridine

To a solution of 2-amino-5-fluoro-3-nitropyridine (0.42 g, 2.3 mmol) and iron powder (1.6 g, 28 mmol) in ethanol (10 ml) were added water (0.5 ml, 28 mmol) and hydrochloric acid (27 μl, 0.32 mmol). The mixture was refluxed for 1 h. An additional amount of iron powder (0.2 g, 3.6 mmol) was added and the mixture was refluxed for 30 min. The reaction mixture was filtered through celite and evaporation under reduced pressure of the solvent gave 0.3 g (100%) of the desired product.

hu 1H-NMR (300 MHz, CDCl$_3$): δ3.55 (bs, 2H), 4.1 (bs, 2H), 6.7 (dd, 1H), 7.5 (d, 1H).

Example 2.6

Synthesis of 8-amino-2,3-dimethyl-6-fluoroimidazo[1,2-a]pyridine

A mixture of 2,3-diamino-5-fluoropyridine (0.3 g, 2.4 mmol) and 3-bromo-2-butanon (0.36 g, 2.4 mmol) in ethanol (20 ml) was refluxed for 10 h. The solvent was evaporated under reduced pressure. The residue was dissolved in methylene chloride and was treated with a bicarbonate solution. The organic layer was separated, dried over sodium sulfate and evaporated under reduced pressure. The residue was purified with column chromatography on silica gel with methanol:methylene chloride (1:20) as eluent to give 0.16 g (37%) of the title compound.

$^1$H-NMR (300 MHz, CDCl$_3$): δ2.3 (s, 3H), 2.4 (s, 3H), 4.6 (bs, 2H), 6.2 (dd, 1H), 7.2 (dd, 1H).

Example 2.7

Synthesis of 8-amino-6-bromo-2,3-dimethylimidazo[1,2-a]pyridine

A solution of 2,3-diamino-5-bromopyridine (4.0 g, 21.29 mmol) and 3-bromo-2-butanone (3.7 g, 24.48 mmol) in ethanol (40 ml) was refluxed overnight. After cooling to room temperature, the crystalline product was filtered and washed with ethanol and ether. The crystals were dissolved in methylene chloride and neutralized by aqueous NaHCO$_3$. The organic layer was separated, dried over Na$_2$SO$_4$ and evaporated in vacuo. Yield 2.3 g.

$^1$H NMR (300 MHz, CDCl$_3$): δ7.39 (d, J=1.7 Hz, 1H), 6.36 (d, J=1.7 Hz, 1H), 4.5 (br s, 2H), 2.35 (s, 3H), 2.3 (s, 3H).

Example 2.8

Synthesis of 3-carboethoxy-8-(dimethylbenzylamino)-2-methylimidazo[1,2-a]pyridine A mixture of 8-amino-3-carboethoxy-2-methylimidazo[1,2-a]pyridine (6.08 g, 27.74 mmol), 2,6-dimethylbenzylchloride (4.5 g, 29.13 mmol), sodium carbonate (4.32 g, 43.7 mmol), sodium iodide (0.7 g) and acetone (120 ml) was stirred for 30 h and the crystalline product was filtered off. The yield was dissolved in dichloromethane filtered and the solvent was evaporated under reduced pressure to give the title product (7.0 g).

$^1$H NMR (300 MHz, CDCl$_3$) δ8.66 (d, J=11 Hz, 1H), 7.16–7.1 (m, 1H), 7.05 (d, J=11 Hz, 2H), 6.87 (t, J=11 Hz, 1H), 6.45 (d, J=11 Hz, 1H), 4.86 ("t", 1H), 4.4 (q, J=7 Hz, 2H) 4.35 (d, J=3.6 Hz, 2H), 2.65 (s, 3H), 2.35 (s, 6H), 1.4 (t, J=7 Hz, 3H).

Example 2.9

Synthesis of 8-amino-6-chloro-2,3-dimethylimidazo[1,2-a]pyridine

A mixture of 2,3-diamino-5-chloropyridine (5.26 g, 36.64 mmol) and 3-bromo-2-butanone (6.2 g, 41.06 mmol) in ethanol (60 ml) was refluxed overnight. After cooling to room temperature, the crystalline product was filtered and washed with ethanol and ether. The crystals were dissolved in methylene chloride and neutralized by aqueous NaHCO$_3$. The organic layer was separated, dried over Na$_2$SO$_4$ and evaporated in vacuo. Yield 3.0 g.

$^1$H NMR (300 MHz, CDCl$_3$): δ7.29 (d, J=1.5 Hz, 1H), 6.26 (d, J=1.5 Hz, 1H), 4.55 (br s, 2H), 2.4 (s, 3H), 2.3 (s, 3H).

Example 2.10

Synthesis of 8-amino-3-carboethoxy-2,6-dimethylimidazo[1,2-a]pyridine

A stirred mixture of 2,3-diamino-5-methyl-pyridine (4.0 g, 32.5 mmol) and (5.9 g, 36.0 mmol) of ethylchloroacetoacetate in 75 ml abs. ethanol was refluxed over night. The ethanol was evaporated under reduced pressure. The residue was dissolved in 2 M HCl and washed 3 times with diethyl ether, pH was adjusted to 9 and extracted 3 times with dichloromethane. The organic layer was dried over anhydrous sodium sulfate and evaporated. The residue was purified by column chromatography on silica gel with dichloromethane:methanol 95:5 as eluent to give the title product 2.0 g (28%).

$^1$H-NMR (300 MHz, CDCl$_3$): δ1.42 (t, 3H), 2.28 (s, 3H), 2.65 (s, 3H), 4.40 (q, 2H), 4.47 (s, 2H), 6.40 (s, 1H), 8.55 (s, 1H).

Example 2.11

Synthesis of 3-carboethoxy-2,6-dimethyl-8-(2,6-dimethylbenzylamino) imidazo[1,2-a]pyridine A stirred mixture of 8-amino-2,6 dimethylimidazol [1,2-a]pyridine (1.2 g, 5.1 mmol), zinc(II)chloride (0.84 g, 6.2 mmol) and 2,6-dimethylbenzaldehyde (0.84 g, 6.2 mmol) in 50 ml methanol was treated with sodium cyanoborohydride (0.39 g, 6.2 mmol) and was refluxed for 5 h. The methanol was evaporated under reduced pressure and the residue was dissolved in dichloromethane and 40 ml 2 M sodium hydroxide. The organic layer was separated, dried over sodium sulfate and evaporated under reduced pressure. The residue was purified by column chromatography on silica gel, eluent petroleum ether (40–60):isopropyl ether 8:2, in yield of 0.8 g, (44%) of the title compound.

$^1$H-NMR (300 MHz, CDCl$_3$): δ1.44 (t, 3H), 2.35 (d, 9H), 2.60 (s, 3H), 4.33 (d, 2H), 4.40 (q, 2H), 4.6 (s, 1H), 6.60 (s, 1H), 7.10 (d, 2H), 7.25 (m, 1H), 8.50 (s, 1H).

Example 2.12

Synthesis of 3-carboethoxy-2,6-dimethyl-8-(2,6-dimethylbenzylamino) imidazo[1,2-a]pyridine A stirred mixture of 8-amino-2,6 dimethylimidazol [1,2-a]pyridine (1.2 g, 5.1 mmol), zinc(II)chloride (0.84 g, 6.2 mmol) and 2,6-dimethylbenzaldehyde (0.84 g, 6.2 mmol) in 50 ml methanol was treated with sodium cyanoborohydride (0.39 g, 6.2 mmol) and was refluxed for 5 h. The methanol was evaporated under reduced pressure and the residue was dissolved in dichloromethane and 40 ml 2 M sodium hydroxide. The organic layer was separated, dried over sodium sulfate and evaporated under reduced pressure. The residue was purified by column chromatography on silica gel, eluent petroleumether (40–60):isopropylether 8:2, in yield of 0.8 g, (44%) of the title compound.

$^1$H-NMR (300 MHz, CDCl$_3$): δ1.44 (t, 3H), 2.35 (d, 9H), 2.60 (s, 3H), 4.33 (d, 2H), 4.40 (q, 2H), 4.6 (s, 1H), 6.60 (s, 1H), 7.10 (d, 2H), 7.25 (m, 1H), 8.50 (s, 1H).

Example 2.13

Synthesis of 3-carboethoxy-2,6-dimethyl-8-(2,6-dimethyl-4-fluorobenzylamino)imidazo[1,2-a]pyridine.

A stirred mixture of (1.1 g, 4.7 mmol) 8-amino-3-carboethoxy-2,6-dimethylimidazo[1,2-a]pyridine (1.2 g, 5.7 mmol) 2,6-dimethyl-4-fluorobenzylbromide, (1.0 g, 7.5 mmol) potassium carbonate and (0.1 g) sodium iodide in 15 ml acetonitrile was refluxed over night. After evaporation of the solvent under reduced pressure the residue was dissolved in dichloromethane and washed with water, the organic layer was separated dried over sodium sulfate and evaporated under reduced pressure. The residue was purified by column chromatography on silica gel, eluent petroleum ether (40–60):isopropyl ether 7:3 to give 0.8 g, (47%) of the title compound.

$^1$H-NMR (300 MHz, CDCl$_3$): δ1.42 (t, 3H), 2.36 (s, 9H), 2.62 (2, 3H), 4.45 (d, 2H), 4.48 (q, 2H), 4.54 (s, 1H), 6.30, (s, 1H), 6.75 (d, 2H), 8.55 (s, 1H).

Example 2.14

Synthesis of 4-chloro-2,6-dimethylbenzylbromide.

4-Chloro-3,5-dimethylbenzene (1.42 g, 0.01 mol) and paraformaldehyde (0.31 g, 0.01 mol) were added to 2 ml of hydrogenbromide (33%) in acetic acid. The mixture was stirred over night at +70° C. The reaction mixture was poured on 25 ml water and the product was extracted with diethyl ether. The organic layer was washed with water. The organic layer was dried (Na$_2$SO$_4$) and evaporated. 1.1 g product (oil) was obtained. The $^1$H-NMR spectrum shows that the substance was a mixture of the title compound and 2-chloro-4,6-dimethylbenzylbromide. The product was used as such without any further purification in the next synthetic step (Example 1.15).

$^1$H-NMR (300 MHz, CDCl$_3$): δ2.28 (s, 6H), 4.51 (s, 2H), 7.04 (s, 2H).

Example 2.15

Synthesis of 3-carboethoxy-2,6-dimethyl-8-(2-ethyl-6-methylbenzylamino)-imidazo[1,2-a]pyridine A mixture of 8-amino-3-carboethoxy-2,6-dimethylimidazo[1,2-a]pyridine (1.4 g, 6 mmol), 2-ethyl-6-methylbenzaldehyde (0.9 g, 6.5 mmol), ZnCl$_2$ (1.0 g, 7.4 mmol), NaB(CN)H$_3$ (0.41 g, 6.5 mmol) and MeOH (30 ml) was refluxed for 5 h. More ZnCl$_2$ (0.2 g) and NaB(CN)H3 (0.1 g) were added. The reaction mixture was refluxed for additional 2 h. Triethylamin (2 ml) was added and the mixture was stirred at R.T for 10 min. The solvent was evaporated under reduced pressure and the residue was purified by column chromatography on silica gel using methylene chloride as eluent. 1.1 g (50%) of the title compound was obtained.

$^1$H-NMR (300 MHz, CDCl$_3$): δ1.25 (t, 3H), 1.45 (t, 3H), 2.30 (s, 6H), 2.6 (s, 3H), 2.75 (q, 2H), 4.35 (d, 2H), 4.45 (q, 2H), 4.85 (bs, 1H), 6.35 (s, 1H), 7.0–7.25 (m, 3H), 8.5 (s, 1H)

Example 2.16

Synthesis of 3-carboethoxy-2,6-dimethyl-8-(2,6-diethylbenzylamino) imidazo[1,2-a]pyridine A stirred mixture of 8-amino-3-carboethoxy-2,6-dimethylimidazo[1,2-a]pyridine (2.02 g, 8.6 mmol), zinc(II) chloride (1.48 g, 10.8 mmol) and 2,6-diethylbenzaldehyde (2.17 g, 13.4 mmol) in 50 ml methanol was treated with sodium cyanoborohydride (0.65 g, 10.3 mmol) and was refluxed overnight. The mixture was allowed to cool and then poured over 80 ml 1M sodium hydroxide. The precipitate formed was filtrated and washed with water and then purified by column chromatography on silica gel with dichloromethane:methanol (95:5) as eluent. The yield was 2.1 g (64%) of the title compound.

$^1$H-NMR (500 MHz, CDCl$_3$): δ1.23 (t, 6H), 1.42 (t, 3H), 2.38 (s, 3H), 2.61 (s, 3H), 2.72 (q, 4H), 4.34 (d, 2H), 4.40 (q, 2H), 4.83 (t, 1H), 6.32 (s, 1H), 7.11 (d, 2H), 7.24 (t, 1H), 8.51 (s, 1H).

Example 2.17

Synthesis of 3-carboethoxy-8-(2,6-dimethyl-4-fluorobenzyloxy)-2-methylimidazo[1,2-a]pyridine A mixture of 3-carboethoxy-8-hydroxy-2-methylimidazo[1,2-a]pyridine (1.5 g, 6.8 mmol), 2,6-dimethyl-4-fluorobenzylbromide (1.6 g, 7.5 mmol), sodium iodide (0.1 g), potassium carbonate (1.9 g, 13.6 mmol) and acetonitrile (50 ml) was refluxed for over night. The solvent was removed in vacuo. The residue was dissolved in CH$_2$Cl$_2$, washed with water, dried over Na$_2$SO$_4$ and evaporated. The residue was chromatographed on silica, eluting with heptane:isopropyl ether(1:2) to give 2.0 g (83%) of the desired product.

$^1$H-NMR (300 MHz, CDCl$_3$): δ1.45 (t, 3H), 2.4 (s, 6H), 2.7 (s, 3H), 4.45 (q, 2H), 5.2 (s, 2H), 6.7–6.9 (m, 4H), 9.0 (d, 2H)

Example 2.18

Synthesis of 8-amino-6-bromo-3-carboethoxy-2-methylimidazo[1,2-a]pyridine

A mixture of 2,3-diamino-5-bromopyridine (2.5 g, 13.31 mmol) and ethyl 2-chloroacetoacetate (2.41 g, 14.64 mmol) in 35 ml abs. Ethanol was refluxed for 14 h. The ethanol was evaporated under reduced pressure. The residue was dissolved in methylene chloride and neutralized by aqueous NaHCO$_3$. The organic layer was separated, dried and evaporated in vacuo. The residue was purified by column chromatography on silica gel with methylene chloride:methanol (100:3.5) as eluent to give 1.55 g (39%) of the title compound.

$^1$H-NMR (300 MHz, CDCl$_3$): δ8.9 (s, 1H), 6.65 (s, 1H), 4.6 (bs, 2H), 4.4 (q, 2H), 2.65 (s, 3H), 1.4 (t, 3H).

Example 2.19

Synthesis of 6-bromo-3-carboethoxy-8-(2,6-dimethyl-4-fluorobenzylamino)-2-methylimidazo[1,2-a]pyridine A mixture of 8-amino-6-bromo-3-carboethoxy-2-methylimidazo[1,2-a]pyridine (2.06 g, 6.91 mmol), 2,6-dimethyl-4-fluorobenzylbromide (1.05 g, 4.48 mmol), sodium iodide (0.45 g), sodium carbonate (2.2 g) and acetone (40 ml) was refluxed for 22 h. The reaction mixture was filtered. The filtered material was washed with CH$_2$Cl$_2$. The methylene chloride solution was washed with water, dried and evaporated in vacuo. The residue was suspended in ethanol/ether and filtered to give 1.15 g (56%) of the title compound.

$^1$H-NMR (300 MHz, CDCl$_3$): δ8.85 (s, 1H), 6.8 (d, 2H), 6.55 (s, 1H), 4.9 (t, 1H), 4.4 (q, 2H), 4.3 (d, 2H), 2.6 (s, 3H), 2.4 (s, 6H), 1.45 (t, 3H).

Example 2.20

Synthesis of 3-(2,6-dimethylbenzyloxy)-5-methyl-2-nitropyridine

To 0.52 g (8.02 mmol) of 87% KOH and 0.15 g q-iodide in 6 ml 95% ethanol was added a solution of 3-hydroxy-5-methyl-2-nitropyridine (1.2 g, 7.79 mmol) in 25 ml of ethanol. To the resulting suspension of the potassium salt was added dropwise a solution of 2,6-dimethyl benzylchloride (1.24 g, 8.02 mmol) in 13 ml of ethanol. The reaction mixture was refluxed for 1 h. More 87% KOH (0.16 g) and 2,6-dimethylbenzylchloride (0.38 g) were added. The reaction mixture was refluxed for additional 70 min. The mixture was filtered and the inorganic salts were washed with ethanol and methylene chloride. The organic layer was evaporated in vacuo. The residue was dissolved in methylene chloride, washed with aqueous NaHCO$_3$, dried and evaporated in vacuo. The residue was suspended in ether/isopropanol and filtered to give 1.72 g (81%) of the title compound.

$^1$H-NMR (500 MHz, CDCl$_3$): δ7.94 (s, 1H), 7.46 (s, 1H), 7.19 (t, 1H), 7.08 (d, 2H), 5.18 (s, 2H), 2.47 (s, 3H), 2.4 (s, 6H).

Example 2.21

Synthesis of 2-amino-3-(2,6-dimethylbenzyloxy)-5-methylpyridine

A mixture of 3-(2,6-dimethylbenzyloxy)-5-methyl-2-nitropyridine (1.9 g, 6.99 mmol), iron powder (6.4 g), concentrated HCl (0.15 ml), water (1.5 ml) and 95% ethanol (35 ml) was refluxed for 1.0 h. The reaction mixture was filtered over celite and the solvent was removed under reduced pressure. The residue was purified by column chromatography on silica gel, using methylene chloride:methanol (100:4) as eluent to give 1.56 g (92%) of the title compound.

¹H-NMR (500 MHz, CDCl₃): δ7.57 s, 1H), 7.2 (t, 1H), 7.09 (d, 2H), 6.95 (s, 1H), 5.02 (s, 2H), 4.45 (bs, 2H), 2.4 (s, 6H), 2.25 (s, 3H).

Example 2.22

Synthesis of 3-carboethoxy-2,6-dimethyl-8-(2,6-dimethylbenzyloxy)imidazo[1,2-a]pyridine A mixture of 2-amino-3-(2,6-dimethylbenzyloxy)-5-methylpyridine (1.0 g, 4.13 mmol) and ethyl 2-chloroacetoacetate (0.79 g, 4.55 mmol) in 20 ml abs. ethanol was refluxed for 19 h. More ethyl 2-chloroacetoacetate (0.25 g) was added. The reaction mixture was refluxed for additional 23 h. The solvent was evaporated in vacuo and the residue was dissolved in methylene chloride and washed with aqueous NaHCO₃. The organic layer was dried and evaporated under reduced pressure. The crude product was purified by column chromatography on silica gel, using methylene chloride:ethyl acetate (100:10) as eluent to give 0.68 g (47%) of the title compound.

¹H-NMR (500 MHz, CDCl₃): δ8.8 (s, 1H), 7.15 (t, 1H), 7.04 (d, 2H), 6.71 (s, 1H), 5.22 (s, 2H), 4.41 (q, 2H), 2.67 (s, 3H), 2.41 (s, 6H), 2.39 (s, 3H), 1.42 (t, 3H).

Example 2.23

Synthesis of 3-carboethoxy-8-(2,6-dimethyl-4-fluoro-benzylamino)-2-methylimidazo[1,2-a]pyridine A stirred mixture of (1.0 g, 4.7 mmol) 8-amino-3-carboethoxy-2-methylimidazo[1,2-a]pyridine (1.2 g, 5.7 mmol) 2,6-dimethyl-4-fluorobenzylbromide, (1.0 g, 7.5 mmol) potassium carbonate and (0.1 g) sodium iodide in 15 ml acetonitrile was refluxed over night. After evaporation of the solvent under reduced pressure the residue was dissolved in dichloromethane and washed with water, the organic layer was separated dried over sodium sulfate and evaporated under reduced pressure. The residue was purified by column chromatography on silica gel, eluent petroleum ether (40–60):isopropyl ether 7:3 to give 1.2 g, (75%) of the title compound.

¹H-NMR (300, MHz, CDCl₃): δ1.45 (t, 3H), 2.35 (s, 6H), 2.65 (s, 3H), 4.40 (d, 2H), 4.40 (q, 2H), 4.85 (t, 1H), 6.40 (d, 1H), 6.75 (d, 2H), 6.85 (t, 1H), 8.70 (d, 1H)

Example 2.24

Synthesis of 2-ethyl-4-fluoro-6-methylbenzylbromide

A mixture of 3-ethyl-1-fluoro-5-methylbenzene (1.1 g, 0.008 mol), paraformaldehyde (1.5 g, 0.05 mol), hydrobromic acid (4.1 ml 0.017 mol) (4.1 M in acetic acid) and acetic acid (2.5 ml) was stirred at ambient temperature for 40 h. To the mixture were water and petroleum ether (40–60) added and the organic layer was separated, washed with water, dried over anhydrous sodium sulfate and evaporated carefully under reduced pressure. The desired product was obtain as a yellow oil (1.3 g, 72%).

¹H-NMR (300 MHz, CDCl₃): δ1.2 (t, 3H), 2.35 (s, 3H), 2.7 (q, 2H), 4.50 (s, 2H), 6.7–6.85 (m, 2H)

Example 2.25

Synthesis of 3-carboethoxy-2,6-dimethyl-8-(2-ethyl-4-fluoro-6-methylbenzylamino)imidazo[1,2-a]pyridine A stirred mixture of (0.7 g, 3.0 mmol) 8-amino-3-carboethoxy-2,6-dimethylimidazo[1,2-a]pyridine, (0.8 g, 3.5 mmol) 2-ethyl-4-fluoro-6-methylbenzylbromide, (0.7 g, 4.8 mmol) potassium carbonate and (0.1 g) sodium iodide in 15 ml acetonitrile was refluxed over night. After evaporation of the solvent under reduced pressure the residue was dissolved in dichloromethane and washed with water, the organic layer was separated dried over sodium sulfate and evaporated under reduced pressure. The residue was purified by column chromatography on silica gel, eluent petroleum ether (40–60):isopropyl ether 7:3 to give 0.4 g, (35%) of the title compound.

¹H-NMR (300 MHz, CDCl₃): δ1.25 (t, 3H), 1.45 (t, 3H), 2.4 (s, 6H), 2.65 (s, 3H), 2.75 (q, 2H), 4.3 (d, 2H), 4.4 (q, 2H), 4.75 (bs, 1H), 6.3 (s, 1H), 6.75–6.85 (m, 2H), 8.5 (s, 1H).

Example 2.26

Synthesis of 3-carboethoxy-8-(2-ethyl-6-methylbenzyloxy)-2-methylimidazo[1,2-a]pyridine A stirred mixture of 3-carboethoxy-8-hydroxy-2-methylimidazo[1,2-a]pyridine (0.92 g, 4.2 mmol), (0.7 g, 4.2 mmol) 2-ethyl-6-methylbenzylchloride (0.7 g, 4.2 mmol), sodium carbonate (1.0 g, 9.4 mmol) and a catalytic amount of potassium iodide in acetonitrile (40 ml) was refluxed for 4 h. After filtration and evaporation of the solvent under reduced pressure the residue was purified by column chromatography on silica gel using methylene chloride:ethylacetate as eluent to give 1.0 g, (68%) of the title compound.

¹H-NMR (300 MHz, CDCl₃): δ1.2 (t, 3H), 1.4 (t, 3H), 2.4 (s, 3H), 2.65 (s, 3H), 2.75 (q, 2H), 4.4 (q, 2H), 5.25 (s, 2H), 6.85–6.9 (m, 2H), 7.05–7.25 (m, 3H), 8.95 (dd, 1H).

Example 2.27

Synthesis of 3-ethyl-1-fluoro-5-methylbenzene

Methyllithium (40 ml, 64 mmol) was added dropwise at 0° C. to a slurry of copper(I)iodide (6.42 g, 33.6 mmol) in diethyl ether (20 ml). After being stirred at 0° C. for 30 minutes, the clear colorless homogeneous cuprate solution was cooled to −78° C. where 3-bromomethyl-1-fluoro-5-methylbenzene (5.15 g, 25.4 mmol) in 10 ml diethyl ether was added. The temperature was allowed to rise slowly. The reaction was quenched at −50° C. with NH₄Cl/NH₃-buffer (50 ml). Extraction with diethyl ether (3×50 ml), brine (1×100 ml). The organic layer was dried over MgSO₄, filtered and the solvents were removed to yield 3.3 g (94%) of the title compound.

hu 1H-NMR (500 MHz, CDCl₃): δ1.22 (t, 3H), 2.32 (s, 3H), 2.60 (q, 2H), 6.69 (d, 2H), 6.78 s, 1H).

Biological Tests

1. In vitro Experiments

Acid Secretion Inhibition in Isolated Rabbit Gastric Glands

Inhibiting effect on acid secretion in vitro in isolated rabbit gastric glands was measured as described by Berglindh et al. (1976) Acta Physiol. Scand. 97, 401–414.

Determination of H⁺,K⁺-ATPase Activity

Preparation of gastric membrane vesicles: Gastric membrane vesicles containing H⁺,K⁺-ATPase were prepared from hog stomachs as previously described by Saccomani et al. (1977) Biochim. Biophys. Acta 465, 311–330.

Permeable vesicles: The membrane fraction was diluted with 1 mM PIPES/Tris, pH 7.4, to obtain a 1% sucrose concentration, homogenized and centrifuged at 100,000×g for 2 hours. The resulting pellet was suspended in water and lyophilized twice.

Determination of H+,K+-ATPase activity: Permeable membrane vesicles (2.5–5 µg) were incubated for 15 min at 37° C. in 18 mM PIPES/Tris buffer, pH 7.4, containing 2 mM MgCl$_2$, 10 mM KCl and 2 mM ATP. The ATPase activity was estimated as release of inorganic phosphate from ATP, as described by LeBel et al. (1978) Anal. Biochem. 85, 86–89.

2. In vivo Experiments

Inhibiting Effect on Acid Secretion in Female Rats

Female rats of the Sprague-Dawly strain are used. They are equipped with cannulated fistulae in the stomach (lumen) and the upper part of the duodenum, for collection of gastric secretions and administration of test substances, respectively. A recovery period of 14 days after surgery is allowed before testing commenced.

Before secretory tests, the animals are deprived of food but not water for 20 h. The stomach is repeatedly washed through the gastric cannula with tap water (+37° C.), and 6 ml Ringer-Glucose given subcutaneously. Acid secretion is stimulated with infusion during 2.5–4 h (1.2 ml/h, subcutaneously) of pentagastrin and carbachol (20 and 110 nmol/kg·h, respectively), during which time gastric secretions are collected in 30-min fractions. Test substances or vehicle are given either at 60 min after starting the stimulation (intravenous and intraduodenal dosing, 1 ml/kg), or 2 h before starting the stimulation (oral dosing, 5 ml/kg, gastric cannula closed). The time interval between dosing and stimulation may be increased in order to study the duration of action. Gastric juice samples are titrated to pH 7.0 with NaOH, 0.1 M, and acid output calculated as the product of titrant volume and concentration.

Further calculations are based on group mean responses from 4–6 rats. In the case of administration during stimulation; the acid output during the periods after administration of test substance or vehicle are expressed as fractional responses, setting the acid output in the 30-min period preceding administration to 1.0. Percentage inhibition is calculated from the fractional responses elicited by test compound and vehicle. In the case of administration before stimulation; percentage inhibition is calculated directly from acid output recorded after test compound and vehicle.

Bioavailability in Rat

Adult rats of the Sprague-Dawley strain are used. One to three days prior to the experiments all rats are prepared by cannulation of the left carotid artery under anaesthesia. The rats used for intravenous experiments are also cannulated in the jugular vein (Popovic (1960) J. Appl. Physiol. 15, 727–728). The cannulas are exteriorized at the nape of the neck.

Blood samples (0.1–0.4 g) are drawn repeatedly from the carotid artery at intervals up to 5.5 hours after given dose. The samples are frozen until analysis of the test compound.

Bioavailability is assessed by calculating the quotient between the area under blood/plasma concentration (AUC) curve following (i) intraduodenal (i.d.) or oral (p.o.) administration and (ii) intravenous (i.v.) administration from the rat or the dog, respectively.

The area under the blood concentration vs. time curve, AUC, is determined by the log/linear trapezoidal rule and extrapolated to infinity by dividing the last determined blood concentration by the elimination rate constant in the terminal phase. The systemic bioavailability (F%) following intraduodenal or oral administration is calculated as F(%)= (AUC (p.o. or i.d.)/AUC (i.v.))×100.

Inhibition of Gastric Acid Secretion and Bioavailability in the Conscious Dog

Labrador retriever or Harrier dogs of either sex are used. They are equipped with a duodenal fistula for the administration of test compounds or vehicle and a cannulated gastric fistula or a Heidenhaim-pouch for the collection of gastric secretion.

Before secretory tests the animals are fasted for about 18 h but water is freely allowed. Gastric acid secretion is stimulated for up to 6.5 h infusion of histamine dihydrochloride (12 ml/h) at a dose producing about 80% of the individual maximal secretory response, and gastric juice collected in consecutive 30-min fractions. Test substance or vehicle is given orally, i.d. or i.v., 1 or 1.5 h after starting the histamine infusion, in a volume of 0.5 ml/kg body weight. In the case of oral administration, it should be pointed out that the test compound is administered to the acid secreting main stomach of the Heidenham-pouch dog.

The acidity of the gastric juice samples are determined by titration to pH 7.0, and the acid output calculated. The acid output in the collection periods after administration of test substance or vehicle are expressed as fractional responses, setting the acid output in the fraction preceding administration to 1.0. Percentage inhibition is calculated from fractional responses elicited by test compound and vehicle.

Blood samples for the analysis of test compound concentration in plasma are taken at intervals up to 4 h after dosing. Plasma is separated and frozen within 30 min after collection and later analyzed. The systemic bioavailability (F%) after oral or i.d. administration is calculated as described above in the rat model.

What is claimed is:

1. A compound of the Formula I

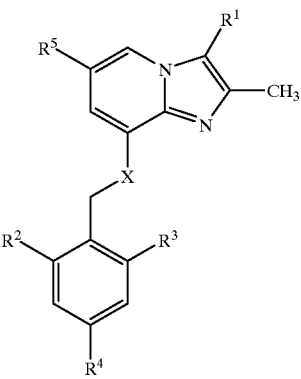

or a pharmaceutically acceptable salt thereof, wherein
$R^1$ is $CH_3$ or $CH_2OH$;
$R^2$ is lower alkyl;
$R^3$ is lower alkyl;
$R^4$ is H or halogen;
$R^5$ is H, halogen, or lower alkyl; and
X is NH or O.

2. A compound according to claim 1 wherein
$R^2$ is $C_1$–$C_4$ alkyl;
$R^3$ is $C_1$–$C_4$ alkyl;
$R^5$ is H, halogen, or $C_1$–$C_4$ alkyl; and
$R^1$, $R^4$ and X are as defined in claim 1.

3. A compound according to claim 1 wherein
$R^2$ is $CH_3$ or $CH_2CH_3$;
$R^3$ is $CH_3$ or $CH_2CH_3$;
$R^4$ is H, Br, Cl or F;
$R^5$ is H, $CH_3$, Br, Cl or F; and
$R^1$ and X are as defined in claim 1.

4. A compound according to claim 3 wherein

R⁵ is H, CH₃, or F; and

R¹, R², R³, R⁴ and X are as defined in claim 3.

5. A compound according to claim 1 which is the compound 8-(2,6-dimethylbenzylamino)-2,3,6-trimethylimidazo[1,2-a]pyridine, or a pharmaceutically acceptable salt thereof.

6. A compound according to claim 1 which is the compound 8-(2,6-dimethylbenzylamino)-3-hydroxymethyl-2-methylimidazo[1,2-a]pyridine, or a pharmaceutically acceptable salt thereof.

7. A compound according to claim 1 which is the compound 2,3-dimethyl-8-(2,6-dimethyl-4-fluorobenzylamino)imidazo[1,2-a]pyridine, or a pharmaceutically acceptable salt thereof.

8. A compound according to claim 1 which is the compound 2,6-dimethyl-8-(2,6-dimethylbenzylamino)-3-hydroxymethyimidazo[1,2-a]pyridine, or a pharmaceutically acceptable salt thereof.

9. A compound according to claim 1 which is the compound 2,6-dimethyl-8-(2,6-dimethyl-4-fluorobenzylamino)-3-hydroxymethylimidazo[1,2-a]pyridine, or a pharmaceutically acceptable salt thereof.

10. A compound according to claim 1 which is the compound 8-(2,6-dimethyl-4-fluorobenzylamino)-2,3,6-trimethylimidazo[1,2-a]pyridine, or a pharmaceutically acceptable salt thereof.

11. A compound according to claim 1 which is the compound 2,3-dimethyl-8-(2,6-dimethyl-4-chlorobenzylamino)imidazo[1,2-a]pyridine, or a pharmaceutically acceptable salt thereof.

12. A compound according to claim 1 which is the compound 2,6-dimethyl-8-(2-ethyl-6-methylbenzylamino)-3-hydroxymethylimidazo[1,2-a]pyridine, or a pharmaceutically acceptable salt thereof.

13. A compound according to claim 1 which is the compound 8-(2,6-diethylbenzylamino)-2,6-dimethyl-3-hydroxymethylimidazo[1,2-a]pyridine, or a pharmaceutically acceptable salt thereof.

14. A compound according to claim 1 which is the compound 8-(2-ethyl-6-methylbenzylamino)-2,3,6-trimethylimidazo[1,2-a]pyridine, or a pharmaceutically acceptable salt thereof.

15. A compound according to claim 1 which is the compound 8-(2,6-dimethyl-4-fluorobenzyloxy)-3-hydroxymethyl-2-methylimidazo[1,2-a]pyridine, or a pharmaceutically acceptable salt thereof.

16. A compound according to claim 1 which is the compound 2,6-dimethyl-8-(2,6-dimethylbenzyloxy)-3-hydroxymethylimidazo[1,2-a]pyridine, or a pharmaceutically acceptable salt thereof.

17. A compound according to claim 1 which is the compound 2,6-dimethyl-8-(2-ethyl-4-fluoro-6-methylbenzylamino)-3-hydroxymethylimidazo[1,2-a]pyridine, or a pharmaceutically acceptable salt thereof.

18. A compound according to claim 1 which is the compound 8-(2-ethyl-4-fluoro-6-methylbenzylamino)-2,3,6-trimethylimidazo[1,2-a]pyridine, or a pharmaceutically acceptable salt thereof.

19. A hydrochloride salt of a compound according to any one of claims 1 to 18.

20. A process for the preparation of a compound according to claim 1 comprising reacting a compound of the Formula II

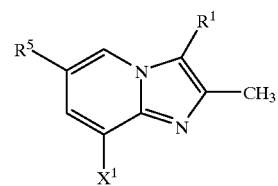

wherein X¹ is NH₂ or OH and R¹ and R⁵ are as defined for Formula I according to claim 1, with a compound of the Formula III

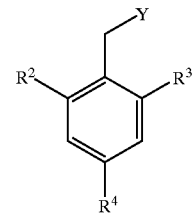

wherein R², R³ and R⁴ are as defined for Formula I and Y is a leaving group, in an inert solvent with or without a base, to form a compound of the Formula I.

21. A process for the preparation of a compound according to claim 1 wherein X is NH, comprising (a) reacting a compound of the Formula IV

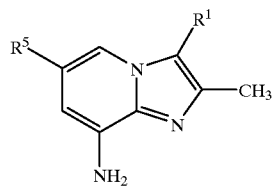

wherein R¹ and R⁵ are as defined for Formula I according to claim 1, with a compound of the Formula V

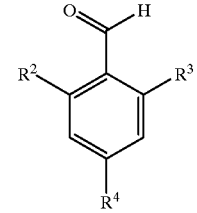

wherein R², R³ and R⁴ are as defined for Formula I, optionally in the presence of a Lewis acid, in an inert solvent to form a compound of the Formula VI

VI

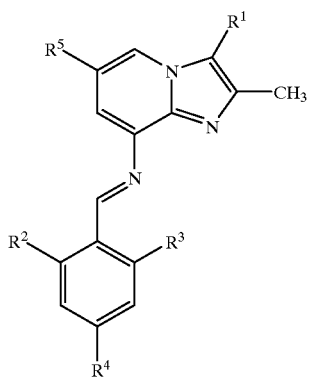

wherein $R^1, R^2, R^3, R^4, R^5$ are as defined for Formula I; and (b) reducing the compound of the Formula VI in an inert solvent under standard conditions to form a compound of the general Formula I wherein X is NH.

22. A process for the preparation of a compound according to claim 1 where $R^1$ is $CH_2OH$ comprising (a) reacting a compound of the Formula VII

VII

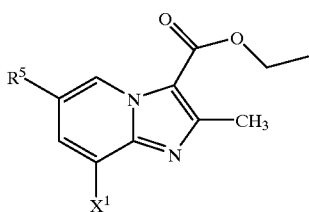

wherein $X^1$ is $NH_2$ or OH and $R^5$ is as defined for Formula I according to claim 1, with a compound of the general Formula III

III

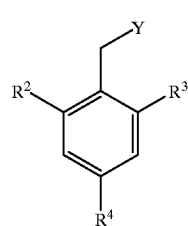

wherein $R^2, R^3$ and $R^4$ are as defined for Formula I and Y is a leaving group, in an inert solvent with or without a base, to form a compound of the Formula VIII,

VIII

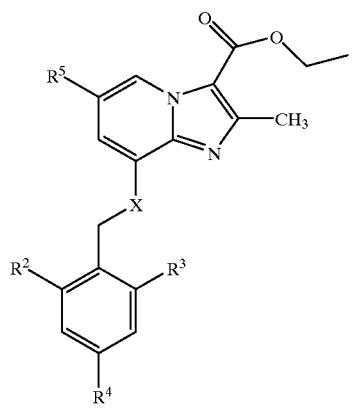

wherein $R^2$, $R^3$, $R^4$, $R^5$ and X is as defined for Formula I; and (b) reducing the compound of Formula VIII in an inert solvent under standard conditions to form a compound of the Formula I wherein $R^1$ is $CH_2OH$.

23. A process for the preparation of a compound according to claim 1, wherein X is NH and $R^1$ is $CH_2OH$, comprising (a) reacting a compound of the Formula IX

IX

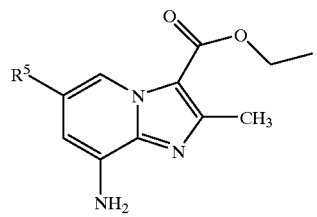

wherein $R^5$ is as defined for Formula I according to claim, with a compound of the Formula V

V

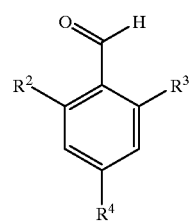

wherein $R^2, R^3$, and $R^4$ is as defined for Formula I, optionally in the presence of a Lewis acid, in an inert solvent to form a compound of the general Formula X

X

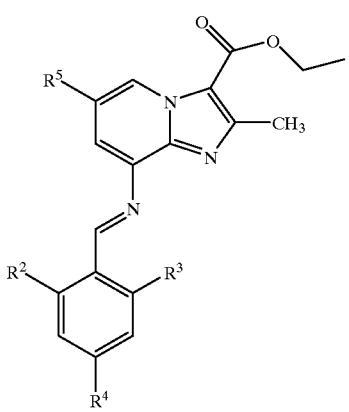

wherein $R^2$, $R^3$, $R^4$ and $R^5$ is as defined for Formula I;
(b) reducing the compound of the Formula X in an inert solvent under standard conditions to form a compound of the Formula XI

XI

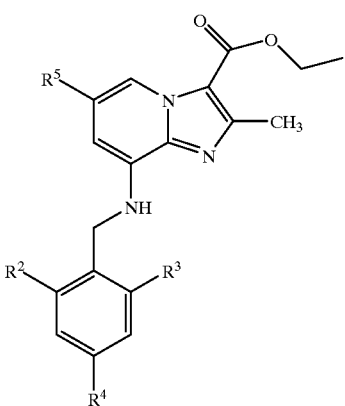

wherein $R^2$, $R^3$, $R^4$ and $R^5$ are as defined for Formula I; and
(c) reducing the compound of the Formula XI in an inert solvent under standard conditions to form a compound of the Formula I wherein X is NH and $R^1$ is $CH_2OH$.

24. A process for the preparation of a compound according to claim 1, wherein X is O and $R^1$ is $CH_2OH$, comprising
(a) reacting a compound of the Formula XII

XII

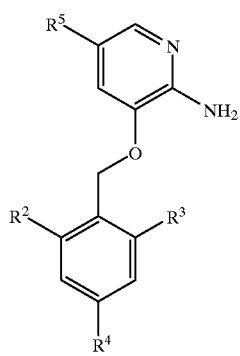

wherein $R^2$, $R^3$, $R^4$ and $R^5$ are as defined for Formula I according to claim 1, with a compound of the formula $CH_3COCH(Z)COOCH_2CH_3$ wherein Z is Br or Cl, in an inert solvent, to form a compound of the Formula XIII

XIII

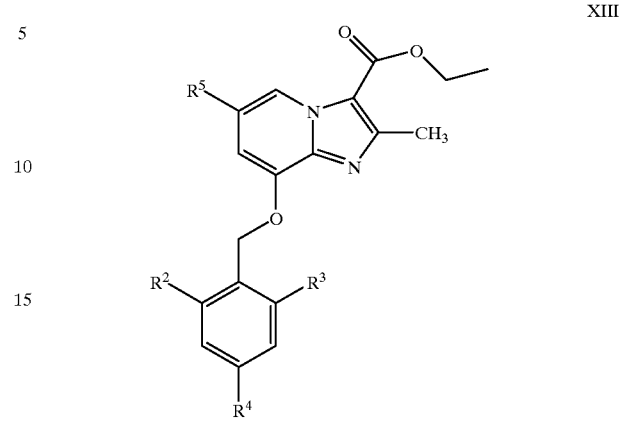

wherein $R^2$, $R^3$, $R^4$ and $R^5$ are as defined for Formula I; and
(b) reducing the compound of the Formula XIII in an inert solvent under standard conditions to form a compound of the general Formula I wherein $R^1$ is $CH_2OH$ and X is O.

25. A pharmaceutical formulation comprising a compound according to any one of claims 1 to 18 and a pharmaceutically acceptable carrier.

26. A method for inhibiting gastric acid secretion which comprises administering to a mammal, in need of such inhibition an effective amount of a compound according to any one of claims 1 to 18.

27. A method for the treatment of gastrointestinal inflammatory diseases which comprises administering to a mammal, in need of such treatment an effective amount of a compound according to any one of claims 1 to 18.

28. A method for the treatment or prophylaxis of conditions involving infection by *Helicobacter pylori* of human gastric mucosa, which comprises administering to a mammal in need of such treatment an effective amount of a compound as claimed in any one of claims 1 to 18.

29. A pharmaceutical formulation for use in the inhibition of gastric acid secretion comprising a compound according to any one of claims 1 to 18 as the active ingredient, and a pharmaceutically acceptable carrier.

30. A pharmaceutical formulation for use in the treatment of gastrointestinal inflammatory diseases comprising a compound according to any one of claims 1 to 18 as the active ingredient, and a pharmaceutically acceptable carrier.

31. A pharmaceutical formulation for use in the treatment or prophylaxis of conditions involving infection by *Helicobacter pylori* of human gastric mucosa, comprising a compound according to any one of claims 1 to 18 as the active ingredient, and a pharmaceutically acceptable carrier.

32. The method according to claim 28, wherein the compound is administered in combination with at least one antimicrobial agent.

33. The pharmaceutical formulation according to claim 31, further comprising at least one antimicrobial agent.

* * * * *

UNITED STATES PATENT AND TRADEMARK OFFICE
CERTIFICATE OF CORRECTION

PATENT NO.   : 6,265,415 B1
DATED        : July 24, 2001
INVENTOR(S)  : Amin et al.

It is certified that error appears in the above-identified patent and that said Letters Patent is hereby corrected as shown below:

Column 37, claim 8,
Line 18, delete "hydroxymethyimidazo" and insert therefor -- hydroxymethylimidazo --.

Column 39, claim 22,
Line 28, delete "where" and insert therefor -- wherein --.

Column 40, claim 23,
Line 46, after "according to claim", insert -- 1 --.
Line 63, delete "general" before "Formula X".

Signed and Sealed this

Twenty-ninth Day of January, 2002

Attest:

JAMES E. ROGAN
*Attesting Officer*   *Director of the United States Patent and Trademark Office*